(12) United States Patent
Inokuma et al.

(10) Patent No.: US 11,320,437 B2
(45) Date of Patent: May 3, 2022

(54) DRIED DYE REAGENT DEVICES AND METHODS FOR MAKING AND USING THE SAME

(71) Applicant: Becton, Dickinson and Company, Franklin Lakes, NJ (US)

(72) Inventors: Margaret Inokuma, San Jose, CA (US); Hema Shah, San Jose, CA (US); Rachna Sehgal, Fremont, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 15/886,725

(22) Filed: Feb. 1, 2018

(65) Prior Publication Data
US 2018/0224460 A1 Aug. 9, 2018

Related U.S. Application Data

(60) Provisional application No. 62/456,557, filed on Feb. 8, 2017.

(51) Int. Cl.
*G01N 33/58* (2006.01)
*G01N 15/14* (2006.01)
*B01L 3/00* (2006.01)

(52) U.S. Cl.
CPC ............ *G01N 33/583* (2013.01); *B01L 3/523* (2013.01); *G01N 15/14* (2013.01); *G01N 33/582* (2013.01);
(Continued)

(58) Field of Classification Search
CPC ................. B01L 3/00; B01L 2300/044; B01L 2300/0681; B01L 2300/0829; B01L 3/523;
(Continued)

(56) References Cited

U.S. PATENT DOCUMENTS 3,759,374 A * 9/1973 Helger ................... G01N 21/03
206/431
3,891,507 A * 6/1975 Breuer ................. G01N 33/523
435/14
(Continued)

FOREIGN PATENT DOCUMENTS

CN 102841195 A 12/2012
CN 104704363 A 6/2015
(Continued)

OTHER PUBLICATIONS

Hedley et al. "Novel Lymphocyte Screening Tube Using Dried Monoclonal Antibody Reagents," Cytometry Part B: Clinical Cytometry, 2015, vol. 88, No. 6, pp. 361-370.
(Continued)

*Primary Examiner* — Christopher L Chin
(74) *Attorney, Agent, or Firm* — Peter W. Schroen; Bret E. Field; Bozicevic, Field & Francis LLP

(57) ABSTRACT

Dried dye reagent devices are provided. Aspects of the devices include a container having positioned therein one or more dried dye compositions that include one or more dyes stably associated with a high surface area solid support. Aspects of the invention further include methods of making and using the devices, e.g., in analyte detection applications, as well as kits containing the devices.

21 Claims, 4 Drawing Sheets

(52) U.S. Cl.
CPC . *B01L 2300/044* (2013.01); *B01L 2300/0681* (2013.01); *B01L 2300/0829* (2013.01)

(58) Field of Classification Search
CPC ............. B01L 3/527; B01L 2300/0609; B01L 2300/0832; B01L 3/5085; B01L 3/50853; B01L 3/52; G01N 15/14; G01N 33/532; G01N 33/543; G01N 33/58; G01N 33/582; G01N 33/583; G01N 33/5304
USPC ........ 436/518, 809; 422/407, 549, 550, 552, 422/553; 424/490, 491; 435/288.4
See application file for complete search history.

(56) References Cited

U.S. PATENT DOCUMENTS

| | | | |
|---|---|---|---|
| 3,992,811 A * | 11/1976 | Yellin | A01G 9/02 47/69 |
| 3,999,948 A * | 12/1976 | Deindoerfer | G01N 33/54366 436/547 |
| 4,142,033 A | 2/1979 | Witenhafer et al. | |
| 4,193,980 A | 3/1980 | Clason et al. | |
| 4,222,379 A * | 9/1980 | Smith | A61J 1/10 604/410 |
| 4,808,539 A * | 2/1989 | Chapoteau | C07D 498/08 436/169 |
| 4,916,078 A | 4/1990 | Klose et al. | |
| 4,919,890 A | 4/1990 | Arai et al. | |
| 5,073,484 A * | 12/1991 | Swanson | G01N 33/558 422/424 |
| 5,213,505 A * | 5/1993 | Laipply | G09B 19/0023 422/513 |
| 5,225,285 A | 7/1993 | Hall et al. | |
| 5,354,654 A * | 10/1994 | Ligler | G01N 33/532 435/5 |
| 5,593,587 A | 1/1997 | Fumihiko et al. | |
| 5,945,341 A * | 8/1999 | Howard, III | G01N 21/8483 436/46 |
| 6,221,655 B1 | 4/2001 | Fung et al. | |
| 6,350,619 B1 | 2/2002 | Mercolino et al. | |
| 7,141,436 B2 | 11/2006 | Gatto-Menking et al. | |
| 7,144,950 B2 | 12/2006 | Bazan et al. | |
| 7,211,443 B2 | 5/2007 | Woudenberg et al. | |
| 7,214,489 B2 | 5/2007 | Bazan et al. | |
| 7,270,956 B2 | 9/2007 | Bazan et al. | |
| 7,332,329 B2 | 2/2008 | Wark et al. | |
| 7,629,448 B2 | 12/2009 | Bazan et al. | |
| 7,666,594 B2 | 2/2010 | Bazan et al. | |
| 7,695,953 B2 | 4/2010 | Gould et al. | |
| 7,807,448 B2 | 10/2010 | Glezer et al. | |
| 7,811,755 B2 | 10/2010 | Bazan et al. | |
| 7,842,475 B2 | 11/2010 | Zheng et al. | |
| 7,867,751 B2 | 1/2011 | Jia et al. | |
| 7,897,684 B2 | 3/2011 | Bazan et al. | |
| 7,914,984 B2 | 3/2011 | Bazan et al. | |
| 7,972,838 B2 | 7/2011 | Korpimaki et al. | |
| 8,101,416 B2 | 1/2012 | Bazan et al. | |
| 8,110,673 B2 | 2/2012 | Bazan et al. | |
| 8,158,444 B2 | 4/2012 | Gaylord et al. | |
| 8,216,530 B2 | 7/2012 | Handique et al. | |
| 8,227,187 B2 | 7/2012 | Bazan et al. | |
| 8,298,834 B2 | 10/2012 | Glezer et al. | |
| 8,338,532 B2 | 12/2012 | Bazan et al. | |
| 8,354,239 B2 | 1/2013 | Gaylord et al. | |
| 8,362,193 B2 | 1/2013 | Gaylord et al. | |
| 8,394,626 B2 | 3/2013 | Ramsey et al. | |
| 8,455,613 B2 | 6/2013 | Gaylord et al. | |
| 8,546,081 B2 | 10/2013 | Bazan et al. | |
| 8,575,303 B2 | 11/2013 | Gaylord et al. | |
| 8,609,044 B2 | 12/2013 | Ullin et al. | |
| 8,617,814 B2 | 12/2013 | Bazan et al. | |
| 8,669,055 B2 | 3/2014 | Bazan et al. | |
| 8,759,444 B2 | 6/2014 | Bazan et al. | |
| 8,802,450 B2 | 8/2014 | Gaylord et al. | |
| 8,835,113 B2 | 9/2014 | Bazan et al. | |
| 8,841,072 B2 | 9/2014 | Bazan et al. | |
| 8,969,509 B2 | 3/2015 | Liu et al. | |
| 8,980,572 B2 | 3/2015 | Wong et al. | |
| 8,993,335 B2 | 3/2015 | Bazan et al. | |
| 9,040,236 B2 | 5/2015 | Hill et al. | |
| 9,085,799 B2 | 7/2015 | Bazan et al. | |
| 9,096,894 B2 | 8/2015 | Iguchi et al. | |
| 9,139,869 B2 | 9/2015 | Gaylord et al. | |
| 9,159,465 B2 | 10/2015 | Bazan et al. | |
| 9,371,559 B2 | 6/2016 | Bazan et al. | |
| 9,383,353 B2 | 7/2016 | Gaylord et al. | |
| 9,442,106 B2 | 9/2016 | Beck et al. | |
| 9,547,008 B2 | 1/2017 | Gaylord et al. | |
| 9,857,365 B2 | 1/2018 | Choi et al. | |
| 9,878,323 B2 | 1/2018 | Glezer et al. | |
| 10,161,935 B2 | 12/2018 | Fujiwara et al. | |
| 2001/0036423 A1 | 11/2001 | Kawasaki et al. | |
| 2002/0001539 A1 * | 1/2002 | DiCesare | B01L 3/5029 422/52 |
| 2002/0015663 A1 * | 2/2002 | Goldstein | A61B 10/0051 422/400 |
| 2003/0006141 A1 | 1/2003 | Gerlach et al. | |
| 2003/0012714 A1 | 1/2003 | Taylor et al. | |
| 2003/0108973 A1 | 6/2003 | Gatto-Menking et al. | |
| 2003/0143755 A1 | 7/2003 | Davis et al. | |
| 2003/0207465 A1 | 11/2003 | Davis et al. | |
| 2003/0219908 A1 | 11/2003 | Davis et al. | |
| 2004/0092036 A1 | 5/2004 | Chen et al. | |
| 2006/0040408 A1 | 2/2006 | Jones et al. | |
| 2006/0182655 A1 | 8/2006 | Zou et al. | |
| 2007/0054341 A1 | 3/2007 | Gatto-Menking et al. | |
| 2007/0202538 A1 | 8/2007 | Glezer et al. | |
| 2007/0243601 A1 | 10/2007 | Korpimaki et al. | |
| 2007/0251337 A1 * | 11/2007 | Reed | G01N 21/6428 73/866 |
| 2008/0194508 A1 * | 8/2008 | Christensen | G01N 33/54393 514/44 R |
| 2008/0241962 A1 * | 10/2008 | Wang | G01N 33/558 436/514 |
| 2008/0274512 A1 | 11/2008 | Squirrell et al. | |
| 2009/0011518 A1 | 1/2009 | Lindberg | |
| 2009/0176213 A1 | 7/2009 | Zheng et al. | |
| 2010/0015628 A1 | 1/2010 | Farchaus et al. | |
| 2010/0172801 A1 | 7/2010 | Pugia et al. | |
| 2010/0184059 A1 | 7/2010 | Lee et al. | |
| 2010/0330684 A1 * | 12/2010 | O'Connor | C12Q 1/40 436/88 |
| 2011/0015091 A1 | 1/2011 | Glezer et al. | |
| 2011/0257374 A1 * | 10/2011 | Gaylord | C07K 16/2812 530/391.5 |
| 2011/0291076 A1 | 12/2011 | Shukla et al. | |
| 2012/0070385 A1 | 3/2012 | Glasky et al. | |
| 2012/0183961 A1 | 7/2012 | Han et al. | |
| 2012/0252986 A1 * | 10/2012 | Liu | C08G 61/02 525/451 |
| 2012/0301943 A1 | 11/2012 | Iguchi et al. | |
| 2013/0052650 A1 | 2/2013 | Kavanagh | |
| 2013/0065788 A1 | 3/2013 | Glezer et al. | |
| 2013/0089853 A1 | 4/2013 | Li et al. | |
| 2014/0271481 A1 * | 9/2014 | Boday | A61K 49/0054 424/9.6 |
| 2014/0302516 A1 | 10/2014 | Chiu et al. | |
| 2014/0319379 A1 * | 10/2014 | Manian | G01N 21/6428 250/459.1 |
| 2015/0125882 A1 | 5/2015 | Bornheimer et al. | |
| 2015/0174547 A1 | 6/2015 | Emans et al. | |
| 2015/0226746 A1 | 8/2015 | Bazan et al. | |
| 2016/0266132 A1 | 9/2016 | Gaylord et al. | |
| 2016/0299164 A1 | 10/2016 | Ackerman et al. | |
| 2016/0320415 A1 | 11/2016 | Manneh | |
| 2016/0341720 A1 | 11/2016 | Bazan et al. | |
| 2016/0349267 A1 | 12/2016 | Gaylord et al. | |
| 2017/0023563 A1 | 1/2017 | Hirano et al. | |
| 2017/0115298 A1 | 4/2017 | Gaylord et al. | |
| 2017/0189902 A1 | 7/2017 | Moran | |
| 2017/0307600 A1 | 10/2017 | Sharkey et al. | |
| 2018/0031554 A1 | 2/2018 | Beck et al. | |

(56) References Cited

U.S. PATENT DOCUMENTS

| | | |
|---|---|---|
| 2018/0078241 A1 | 3/2018 | Moga et al. |
| 2018/0143108 A1 | 5/2018 | Madsen et al. |
| 2018/0154353 A1 | 6/2018 | Glezer et al. |
| 2018/0224460 A1 | 8/2018 | Inokuma et al. |
| 2019/0004075 A1 | 1/2019 | Ackerman et al. |

FOREIGN PATENT DOCUMENTS

| | | |
|---|---|---|
| CN | 105358977 A | 2/2016 |
| EP | 0225703 | 6/1987 |
| EP | 0225703 A2 | 6/1987 |
| EP | 0464942 | 1/1992 |
| EP | 0464942 A1 | 1/1992 |
| JP | H0374405 | 3/1991 |
| JP | 2013007751 A | 1/2013 |
| JP | 2013165709 A | 8/2013 |
| JP | 2014001949 A | 1/2014 |
| JP | 2015102337 A | 6/2015 |
| JP | 2015528114 A | 9/2015 |
| KR | 101495631 | 2/2015 |
| WO | WO 2004/001379 A2 | 12/2003 |
| WO | WO 2004/077014 A2 | 9/2004 |
| WO | WO 2004/092324 A2 | 10/2004 |
| WO | WO 2005/086617 A2 | 9/2005 |
| WO | WO 2006/003423 A2 | 1/2006 |
| WO | WO2006003423 | 1/2006 |
| WO | WO 2006/074471 A2 | 7/2006 |
| WO | WO 2006/074482 A2 | 7/2006 |
| WO | WO 2006/083932 A2 | 8/2006 |
| WO | WO 2008/100344 A2 | 8/2008 |
| WO | WO 2010/151807 A1 | 12/2010 |
| WO | WO 2011/091086 A1 | 7/2011 |
| WO | WO2011105507 A1 | 6/2013 |
| WO | WO2017123622 A1 | 7/2017 |
| WO | WO/2017/222998 A1 | 12/2017 |

OTHER PUBLICATIONS

Thakar et al. "CD4 estimating reagents in dry format are compatible with conventional flow cytometer; FACSCalibur for estimation of absolute CD4 count & percentages," The Indian Journal of Medical Research, vol. 137, No. 2, Feb. 2013, pp. 346-355.

"ReaPan 34845", Jan. 30, 2013 (Jan. 30, 2013) pp. 1-2. Retrieved from the Internet: URL:http://www.demo.reametrix.comjdownload/QMS/Product Inserts/ReaPan34845.pdf.

Communication the extended European search report for European Patent Application No. 17786484.0, dated Oct. 24, 2019, 6 pages.

Wang, "Clinical Flow Cytometry", Jianzhong Wang, p. 244 245, Shanghai Science and Technology Press, Aug. 2005.

* cited by examiner

DRIED DYE REAGENT DEVICES AND METHODS FOR MAKING AND USING THE SAME

CROSS-REFERENCE TO RELATED APPLICATION

Pursuant to 35 U.S.C. § 119(e), this application claims priority to the filing date of U.S. Provisional Patent Application Ser. No. 62/456,557 filed Feb. 8, 2017; the disclosure of which application is incorporated herein by reference.

INTRODUCTION

Assays for determining the presence and concentration of analytes in a liquid biological sample often rely on the specific binding of a detectable label (e.g., comprising a dye moiety conjugated to a specific binding member, such as an antibody) to the target analyte. The detectable label may be a marker that can be visualized either by an unaided eye or detectable by spectroscopy, such as fluorescence or UV-vis spectroscopy. Typically, fluorescent dyes may be used as the detectable label, where the fluorescent dye includes a particular fluorochrome. A fluorochrome may have a certain properties, such as its absorption spectrum, its extinction coefficient at a wavelength convenient for excitation, its emission spectrum, and its quantum efficiency. Quantum efficiency is the number of photons emitted for every photon absorbed.

The properties of a fluorochrome may depend on its surrounding environment. For example, some fluorochromes, such as fluorescein, are sensitive to pH. Fluorescence can also be quenched by an interaction with another molecule in which the emission energy of the dye is dissipated by a non-radiative transition. In some cases, the detectable fluorescence of a fluorochrome can be quenched by interactions between the molecules of another fluorochrome, such as a fluorochrome of another dye. This effect can be observed as an undesirable dye-dye interaction where the fluorescence of a dye is significantly less than would be expected as compared to the dye's fluorescence in the absence of other interfering dyes.

SUMMARY

Dried dye reagent devices are provided. Aspects of the devices include a container having positioned therein one or more dried dye compositions that include one or more dyes stably associated with a high surface area solid support. Aspects of the invention further include methods of making and using the devices, e.g., in analyte detection applications, as well as kits containing the devices.

DETAILED DESCRIPTION

Figure 1:
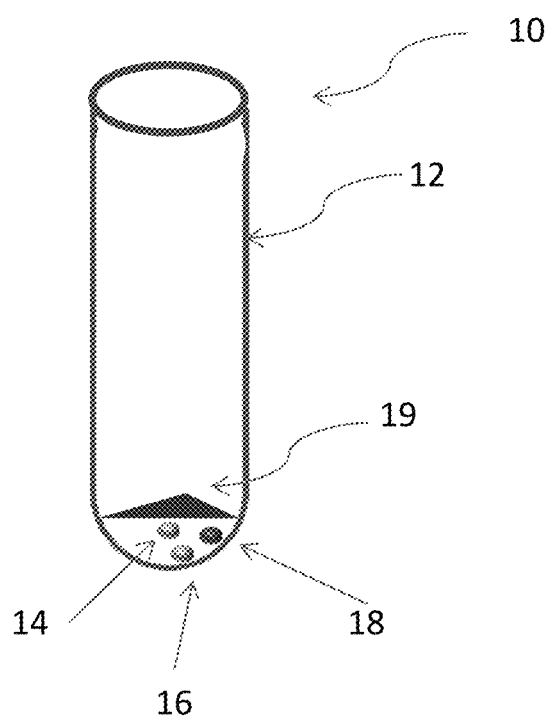
FIG. 1 provides an illustration of a multiplex dried dye reagent device according to an embodiment of the invention.

Dried dye reagent devices are provided. Aspects of the devices include a container having positioned therein one or more dried dye compositions that include one or more dyes stably associated with a high surface area solid support. Aspects of the invention further include methods of making and using the devices, e.g., in analyte detection applications, as well as kits containing the devices.

Before embodiments of the present disclosure are described in greater detail, it is to be understood that these embodiments are not limited to the particular embodiments described, as such may vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the embodiments of the present disclosure. The upper and lower limits of these smaller ranges may independently be included in the smaller ranges and are also encompassed within the embodiments of the present disclosure, subject to any specifically excluded limit in the stated range. Where the stated range includes one or both of the limits, ranges excluding either or both of those included limits are also included in the embodiments of the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the embodiments of the present disclosure. Any recited method can be carried out in the order of events recited or in any other order which is logically possible.

As summarized above, the present disclosure provides dried dye reagent devices that include a container having positioned therein one or more dried dye compositions that include a dye stably associated with a high surface area solid support. In further describing various embodiments of the invention, the reagent devices are first reviewed in greater detail. Next, methods of using the reagent devices are described. In addition, methods of making the reagent devices, as well as kits that include the reagent devices, are described further.

Dried Dye Reagent Devices

Aspects of the present disclosure include dried dye reagent devices. In certain embodiments, the devices are useful in assays, for example assays of a liquid sample, such as a biological sample, e.g., for the presence of one or more analytes in the sample. Dried dye reagent devices according to certain embodiments of the present disclosure include a container having positioned therein one or more dried dye compositions that include a dye stably associated with a high surface area solid support.

The container may vary widely, depending on the particular embodiment and use for which it is configured. The size of the liquid container may. For instance, the container may have a volume (e.g., be configured to hold a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the container is configured to hold a volume (e.g., a volume of a liquid) ranging from 0.1 ml to 200 ml.

The shape of the container may also vary and may depend on the use of the dried dye reagent device. For example, as described herein, the dried dye reagent device may find use in an assay, such as an assay of a liquid sample (e.g., a biological sample). In these cases, the container may be configured in a shape that is compatible with the assay and/or the method or other devices used to perform the assay. For instance, the container may be configured in a shape of typical laboratory equipment used to perform the assay or in a shape that is compatible with other devices used to perform the assay. In some instances the container may be configured to store multiple dried dye compositions, e.g., the container may be storage container for multiple dried dye compositions, where the storage container may be configured so that one or more dried dye reagent compositions may be readily removed from the container at a time of use, e.g., for performance of a particular assay.

In some embodiments, the container is a liquid container, such as a vial or a test tube. In certain cases, the liquid container is a vial. In certain cases, the liquid container is a test tube. As described above, the liquid container may be configured to hold a volume (e.g., a volume of a liquid). In embodiments where the liquid container is a vial or a test tube, the liquid container may be configured to hold a volume (e.g., a volume of a liquid) ranging from 0.1 ml to 1000 ml, such as from 0.5 ml to 900 ml, or 0.5 ml to 800 ml, or 0.5 ml to 700 ml, or 0.5 ml to 600 ml, or 0.5 ml to 500 ml, or 0.5 ml to 400 ml, or 0.5 ml to 300 ml, or 0.5 ml to 200 ml, or 0.5 ml to 100 ml, or 0.5 ml to 50 ml, or 0.5 ml to 25 ml, or 0.5 ml to 10 ml, or 0.5 ml to 5 ml, or 1 ml to 5 ml. In certain instances, the vial or test tube is configured to hold a volume (e.g., a volume of a liquid) ranging from 0.5 ml to 5 ml.

In other embodiments, the container is a well of a single well or a multi-well plate. Where the container is a well of a multi-well plate, the multi-well plate may include a plurality of liquid containers (e.g., wells), such as 2 or more, or 10 or more, or 50 or more, or 75 or more, or 100 or more, or 300 or more, or 500 or more, or 750 or more, or 1000 or more or 1500 or more, or 2000 or more liquid containers (e.g., wells). Examples of solid supports configured as multi-well plates may include, for example, 6, 12, 24, 96, 384 or 1536 liquid containers (e.g., wells). In embodiments where the liquid container is a well of a multi-well plate, an individual well may be configured to hold a volume (e.g., a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the vial or test tube is configured to hold a volume (e.g., a volume of a liquid) ranging from 0.1 ml to 25 ml.

A container of the invention may also be configured as a bottle, cannister or analogous structure, e.g., configured to hold multiple dried dye compositions. In such instances the bottle, cannister or analogous structure may have a volume ranging from ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the vial or test tube is configured to hold a volume (e.g., a volume of a liquid) ranging from 0.1 ml to 25 ml.

In some instances, dried dye composition is not stably associated with any surface of the container, such as any interior wall location of the container. In these instances, as the dryed dye composition is not stably associated, it moves freely relative the surfaces of the container. In such instances, the dried dye composition is not bound in any way to a surface of the container. Where desired, the container is fabricated from a material that is compatible with the liquid sample and/or reagent(s) or analyte(s) in contact with the multiplex dye device, e.g., during use. Examples of suitable container materials for the devices include, but are not limited to, glasses and plastics. For example, the container may be composed of a glass, such as, but not limited to, silicate glass, borosilicate glass, sodium borosilicate glass (e.g., PYREX™), fused quartz glass, fused silica glass, and the like. Other examples of suitable materials for the containers include polymeric materials, e.g., plastics, such as, but not limited to, polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), and the like. The container may be clear or colored, e.g., amber, as desired, and in some instances may be configured to block transmission of light, i.e., it may be opaque.

In some embodiments, the liquid container may be sealed. That is, the liquid container may include a seal that substantially prevents the contents of the liquid container (e.g., liquid inside the liquid container) from exiting the liquid container. The seal of the liquid container may also substantially prevent other substances from entering the liquid container. For example, the seal may be a water-tight seal that substantially prevents liquids from entering or exiting the container, or may be an air-tight seal that substantially prevents gases from entering or exiting the container. In some instances, the seal is a removable or breakable seal, such that the contents of the liquid container may be exposed to the surrounding environment when so desired, e.g., if it is desired to remove a portion of the contents of the liquid container. In some instances, the seal is made of a resilient material to provide a barrier (e.g., a water-tight and/or air-tight seal) for retaining a sample in the container. Particular types of seals include, but are not limited to: films, such as polymer films; caps, etc., depending on the type of container. Suitable materials for the seal include, for example, rubber or polymer seals, such as, but not limited to, silicone rubber, natural rubber, styrene butadiene rubber, ethylene-propylene copolymers, polychloroprene, polyacrylate, polybutadiene, polyurethane, styrene butadiene, and the like, and combinations thereof, metals and metal alloys, etc. In certain embodiments, the seal is a septum pierceable by a needle, syringe, or cannula. The seal may also provide convenient access to a sample in the container, as well as a protective barrier that overlies the opening of the container. In some instances, the seal is a removable seal, such as a threaded or snap-on cap or other suitable sealing element that can be applied to the opening of the container. For instance, a threaded cap can be screwed over the opening before or after a sample has been added to the container.

In some instances the reagent device is a dispenser, where the dispenser holds multiple numbers, e.g., 2 to 200, such as 5 to 100, including 10 to 50, dried dye compositions. The dispenser may be configured to dispense one or more reagent compositions upon actuation, e.g., via manual depression of an actuator. Any convenient dispenser may be employed. Examples of dispensers that may be adapted for use as dispensers of dried reagent compositions as described herein include, but are not limited to, those described in U.S. Pat. Nos. 5,377,865; 4,591,556; 4,324,859; 4,215,799 and 3,934,753; the disclosures of which are herein incorporated by reference. Commercially available disc dispensers that may be employed in devices according to embodiments of the invention include those BD BBLTM Sensi-Disc Dispensers and containers used therewith (Becton, Dickinson and Company).

As summarized above, the containers of the dried dye reagent devices of the invention include one or more dried dye compositions that include a dye stably associated with a high surface area solid support. As such, the containers include at least a first dried dye composition that includes a dye stably associated with a high surface area solid support. The total number of dried dye compositions may vary as desired. A given dried dye reagent device may include 2 or more dried dye compositions, or 3 or more, or 4 or more, or 5 or more, or 6 or more, or 7 or more, or 8 or more, or 9 or more, or 10 or more, or 11 or more, or 12 or more, or 13 or more, or 14 or more, or 15 or more, 16 or more, or 17 or more, or 18 or more, or 19 or more, or 20 or more, or 25 or more, or 30 or more, or 35 or more, or 40 or more, or 45 or more, or 50 or more dried dye compositions. In some embodiments, the reagent device includes 2 to 200 dried dye compositions, such as 2 to 100 dried dye compositions, including 2 to 50 dried dye compositions, such as 2 to 40, or 2 to 30 or 2 to 20 or 2 to 15, or 2 to 10, or 2 to 7, or 2 to 5 dried dye compositions. For example, the device may include 2, or 3, or 4, or 5, or 6, or 7, or 8, or 9, or 10, or 11, or 12, or 13, or 14, or 15, or 16, or 17, or 18, or 19, or 20 dried dye compositions.

In a given container, the dried dye compositions may be identical or at least two of the dried dye compositions in the container may be distinct from each other. In certain cases, the reagent device includes 2 distinct dried dye compositions. In certain cases, the reagent device includes 5 distinct dried dye compositions. In certain cases, the reagent device includes 7 distinct dried dye compositions. In certain cases, the reagent device includes 10 distinct dried dye compositions. Any two dried dye compositions are considered to be distinct if their dye components differ from each other by one or more of molecular formula, excitation maximum and emission maximum. As such, different or distinct dye compositions may differ from each other in terms of chemical composition and/or in terms of one or more properties of the dyes. For instance, different dye compositions may differ from each other by at least one of excitation maxima and emission maxima. In some cases, different dye compositions differ from each other by their excitation maxima. In some cases, different dye compositions differ from each other by their emission maxima. In some cases, different dye compositions differ from each other by both their excitation maxima and emission maxima. As such, in embodiments that include first and second dyes, the first and second dyes may differ from each other by at least one of excitation maxima and emission maxima. For example, the first and second dyes may differ from each other by excitation maxima, by emission maxima, or by both excitation and emission maxima. Additional dye compositions may be included in the reagent device, where each of the dye compositions in the reagent device differ from each other as described above. A given pair of dyes may be considered distinct if they differ from each other in terms of excitation or emission maximum, where the magnitude of such difference is, in some instances, 5 nm or more, such 10 nm or more, including 15 nm or more, wherein in some instances the magnitude of the difference ranges from 5 to 400 nm, such as 10 to 200 nm, including 15 to 100 nm, such as 25 to 50 nm.

As summarized above, the dried dye compositions include one or more dyes stably associated with a high surface area solid support. High surface area solid supports are solid supports having a surface area of 0.5 mm$^2$ or more, such as 2 mm$^2$ or more, including 5 mm$^2$ or more, e.g., as determined using a Vertex system or equivalent.

The dimensions of the high surface area solid supports may vary, as desired, where in some instances the dimensions are determined with respect to the dimensions of the container into which the supports are to be placed. In some instances, the high surface area solids supports have a longest dimension ranging from 1 mm to 5 mm, such as 1 mm to 2 mm. The shapes of the high surface area solids supports may also vary as desired. In some instances high surface area solid supports may be shaped or configured as discs, spheres, ovates, cubes, blocks, cones, etc., as well as irregular shapes. The mass of the high surface area solid supports may vary, ranging in some instances from 0.5 mg to 12 mg, In some instances, the high surface area solids supports are porous. In such instances, the high surface area solid supports may have a porosity ranging from 5µ to 90µ, such as 20µ to 50µ e.g., as determined using a Capillary Flow Porometer or equivalent.

The high surface area solid supports may be fabricated from any convenient material. Suitable materials include, but are not limited to, glass materials (e.g., silicates), ceramic materials (e.g., calcium phosphates), metallic materials, and polymeric materials, etc. such as for example, polyethylene, polypropylene, polytetrafluoroethylene, polyvinylidine fluoride, and the like.

In some instances, the high surface area solid supports are porous matrices as described in U.S. Published Application Publication No. U.S. Pat. No. 9,797,899, the disclosure of which is herein incorporated by reference. As such, a surface area solid support may be any suitable macroporous and/or microporous substrate, where suitable macroporous and/or microporous substrates include, but are not limited to, ceramic matrices, frits, such as fritted glass, polymeric matrices as well as metal-organic polymeric matrices. In some embodiments, the porous matrix is a frit. The term "frit" is used herein in its conventional sense to refer to the porous composition formed from a sintered granulated solid, such as glass. Frits may have a chemical constituent which vary, depending on the type of sintered granulate used to prepare the frit, where frits that may be employed include, but are not limited to, frits composed of aluminosilicate, boron trioxide, borophosphosilicate glass, borosilicate glass, ceramic glaze, cobalt glass, cranberry glass, fluorophosphate glass, fluorosilicate glass, fuzed quartz, germanium dioxide, metal and sulfide embedded borosilicate, leaded glass, phosphate glass, phosphorus pentoxide glass, phosphosilicate glass, potassium silicate, soda-lime glass, sodium hexametaphosphate glass, sodium silicate, tellurite glass, uranium glass, vitrite and combinations thereof. In some embodiments, the porous matrix is a glass frit, such as a borosilicate, aluminosilicate, fluorosilicate, potassium silicate or borophosphosilicate glass frit.

In some embodiments, the porous matrix is a porous organic polymer. Porous organic polymers of interest vary depending on the sample volume, components in the sample as well as assay reagent present and may include but are not limited to porous polyethylene, polypropylene, polytetrafluoroethylene (PTFE), polyvinylidene fluoride (PVDF), ethyl vinyl acetate (EVA), polycarbonate, polycarbonate alloys, polyurethane, polyethersulfone, copolymers and combinations thereof. For example, porous polymers of interest include homopolymers, heteropolymers and copolymers composed of monomeric units such as styrene, monoalkylene allylene monomers such as ethyl styrene, α-methyl styrene, vinyl toluene, and vinyl ethyl benzene; (meth)acrylic esters such as methyl(meth)acrylate, ethyl (meth)acrylate, butyl(meth)acrylate, isobutyl(meth)acrylate, isodecyl(meth)acrylate, 2-ethylhexyl (meth)acrylate, lauryl (meth)acrylate, stearyl(meth)acrylate, cyclohexyl(meth) acrylate, and benzyl(meth)acrylate; chlorine-containing monomers such as vinyl chloride, vinylidenechloride, and chloromethylstyrene; acrylonitrile compounds such as acrylonitrile and methacrylonitrile; and vinyl acetate, vinyl propionate, n-octadecyl acrylamide, ethylene, propylene, and butane, and combinations thereof.

In some embodiments, the porous matrix is a metal organic polymer matrix, for example an organic polymer matrix that has a backbone structure that contains a metal such as aluminum, barium, antimony, calcium, chromium, copper, erbium, germanium, iron, lead, lithium, phosphorus, potassium, silicon, tantalum, tin, titanium, vanadium, zinc or zirconium. In some embodiments, the porous metal organic matrix is an organosiloxane polymer including but not limited to polymers of methyltrimethoxysilane, dimethyldimethoxysilane, tetraethoxysilane, methacryloxypropyltrimethoxysilane, bis(triethoxysilyl)ethane, bis(triethoxysilyl)butane, bis(triethoxysilyl)pentane, bis(triethoxysilyl) hexane, bis(triethoxysilyl)heptane, bis(triethoxysilyl) octane, and combinations thereof.

In some embodiments, the high surface area solid support may be particle, such as a bead. Particles, such as beads, include structures having a diameter in the nanometer to micrometer range, such as from 0.01 to 1,000 μm in diameter, for example from 0.1 to 100 μm in diameter, and including from 1 to 100 μm in diameter, and, for use in flow cytometry, including from about 1 to 10 μm in diameter. Such particles can be of any shape, and in some instances are approximately spherical. Such particles can be made of any appropriate material (or combinations thereof), including, but not limited to polymers such as polystyrene; polystyrene which contains other co-polymers such as divinylbenzene; polymethylmethacrylate (PMMA); polyvinyltoluene (PVT); copolymers such as styrene/butadiene, styrene/vinyltoluene; latex; glasses; or other materials, such as silica (e.g., $SiO_2$). Particles suitable for use in the present invention may be obtained from commercial sources. Unstained microspheres in a variety of sizes and polymer compositions that are suitable for the preparation of fluorescent microparticles of the invention are available from a variety of sources, including: Bangs Laboratories (Carmel, Ind.), Interfacial Dynamics Corporation (Portland, Oreg.), Dynal (Great Neck, N.Y.), Polysciences (Warrington, Pa.), Seradyne (Indianapolis, Ind.), Magsphere (Pasadena, Calif.), Duke Scientific Corporation (Palo Alto, Calif.), Spherotech Inc. (Libertyville, Ill.) and Rhone-Poulenc (Paris, France). Chemical monomers for preparation of microspheres are available from numerous sources. In some instances, the surface of the particles may be modified, e.g., to provide for binding, such as covalent or non-covalent binding, with a reagent, such as a dye, e.g., as described below. Of interest in some embodiments are particles, e.g., beads, such as glass beads, having low or no auto-fluorescence.

As reviewed above, the dye compositions of the solid support are dried dye compositions. A dried dye composition is a dye composition that includes a low amount of solvent. For example, dried dye compositions may include a low amount of a liquid, such as water. In some cases, a dried dye composition includes substantially no solvent. For instance, dried dye compositions may include substantially no liquid, such as water. In certain embodiments, a dried dye composition includes 25 wt % or less solvent, such as 20 wt % or less, or 15 wt % or less, or 10 wt % or less, or 5 wt % or less, or 3 wt % or less, or 1 wt % or less, or 0.5 wt % or less solvent. In some cases, a dried dye composition is not a fluid. In some cases, a dried dye composition is substantially a solid. For example, a dried dye composition may have a high viscosity, such as a viscosity of 10,000 cP or more, or 25,000 cP or more, or 50,000 cP or more, or 75,000 cP or more, or 100,000 cP or more, or 150,000 cP or more, or 200,000 cP or more, or 250,000 cP or more at standard conditions.

The dried dye compositions may include one or more non-dye materials. When present, the non-dye material is a material compatible with other assay components (e.g., reagents, buffers, analytes, etc.) that may be present in the reagent device during use. The non-dye material may be substantially inert with respect to the other assay components (e.g., reagents, buffers, analytes, etc.) that may be present in the reagent device during use such that there is no significant reaction between the non-dye material and the other assay components. Examples of non-dye materials include, but are not limited to, stabilizers, buffers, soluble inert materials (e.g., aqueous soluble inert materials), and the like. Stabilizers of interest include, but are not limited to: sugars and polyalcohols. Sugars and polyalcohols suitable for use in lyophilized dye compositions include sugars that are compatible with the other reagents, buffers, dyes and sample components being used. Examples of suitable sugars include, but are not limited to, sucrose, maltose, trehalose, 2-hydroxypropyl-beta-cyclodextrin (β-HPCD), lactose, glucose, fructose, galactose, glucosamine, and the like, and combinations thereof. In certain instances, the sugar is a disaccharide. For example, the disaccharide may be sucrose. Examples of suitable polyalcohols include, but are not limited to, mannitol, glycerol, erythritol, threitol, xylitol, sorbitol, and the like, and combinations thereof. Non-dye materials may include, for example, bovine serum albumin (BSA), sodium azide, glycerol, phenylmethanesulfonyl fluoride (PMSF), ethylenediaminetetraacetic acid (EDTA), buffered citrate, phosphate buffered saline (PBS), sodium chloride, paraformaldehyde, and the like, and combinations thereof.

In some instances, the dried dye compositions are lyophilized dye compositions. In certain cases, a lyophilized dye composition is a dye composition where water has been removed from the dye composition by sublimation, where the water in the dye composition undergoes a phase transition from a solid to a gas. For example, a lyophilized dye composition may be a dye composition where water has been removed from the composition by freezing the dye composition (e.g., freezing water in the dye composition) and then reducing the pressure surrounding the dye composition such that the water in the dye composition undergoes sublimation. In certain instances, a lyophilized dye composition includes water in a low amount, such as 25% or less, or 20% or less, or 15% or less, or 10% or less, or 9% or less, or 8% or less, or 7% or less, or 6% or less, or 5% or less, or 4% or less, or 3% or less, or 2% or less, or 1% or less, or 0.5% or less, or 0.25% or less, or 0.1% or less water as measured by Karl Fischer (KF) titration. In some cases, a lyophilized dye composition has 3% or less water as measured by Karl Fischer titration. In some cases, a lyophilized dye composition has 1% or less water as measured by Karl Fischer titration. In some cases, a lyophilized dye composition has 0.5% or less water as measured by Karl Fischer titration. Lyophilized dye compositions may include additives and/or excipients, such as a stabilizer. In some cases, the lyophilized dye composition includes a stabilizer, such as a sugar or a polyalcohol. Sugars and polyalcohols suitable for use in lyophilized dye compositions include sugars that are compatible with the other reagents, buffers, dyes and sample components being used. Examples of suitable sugars include, but are not limited to, sucrose, maltose, trehalose, 2-hydroxypropyl-beta-cyclodextrin (β-HPCD), lactose, glucose, fructose, galactose, glucosamine, and the like, and combinations thereof. In certain instances, the sugar is a disaccharide. For example, the disaccharide may be sucrose. Examples of suitable polyalcohols include, but are not limited to, mannitol, glycerol, erythritol, threitol, xylitol, sorbitol, and the like, and combinations thereof.

As summarized above, the dye in the dye composition is stably associated with the high surface area solid support. By stably associated is meant that the dye does not readily dissociate from the solid support prior to contact with a liquid medium, e.g., an aqueous medium. As such, when present in the container in a dried state (e.g., prior to use in an assay), the dye remains associated with its high surface area solid support.

The dye in the dye composition may be used as a detectable label. In certain cases, the dye includes detectable moieties or markers that are detectible based on, for example, fluorescence emission maxima, fluorescence polarization, fluorescence lifetime, light scatter, mass, molecular mass, or combinations thereof. In certain embodiments, the detectable label is a fluorophore (i.e., a fluorescent label, fluorescent dye, etc.). Fluorophores of interest may include, but are not limited to, dyes suitable for use in analytical applications (e.g., flow cytometry, imaging, etc.).

In some instances, the fluorophore (i.e., dye) is a polymeric dye (e.g., a fluorescent polymeric dye). Fluorescent polymeric dyes that find use in the subject methods and systems are varied. In some instances of the method, the polymeric dye includes a conjugated polymer. Conjugated polymers (CPs) are characterized by a delocalized electronic structure which includes a backbone of alternating unsaturated bonds (e.g., double and/or triple bonds) and saturated (e.g., single bonds) bonds, where π-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some instances, the polymeric dye includes a CP that has a rigid rod structure. The structural characteristics of the polymeric dyes can have an effect on the fluorescence properties of the molecules.

Any convenient polymeric dye may be utilized in the subject devices and methods. In some instances, a polymeric dye is a multichromophore that has a structure capable of harvesting light to amplify the fluorescent output of a fluorophore. In some instances, the polymeric dye is capable of harvesting light and efficiently converting it to emitted light at a longer wavelength. In some cases, the polymeric dye has a light-harvesting multichromophore system that can efficiently transfer energy to nearby luminescent species (e.g., a "signaling chromophore"). Mechanisms for energy transfer include, for example, resonant energy transfer (e.g., Forster (or fluorescence) resonance energy transfer, FRET), quantum charge exchange (Dexter energy transfer), and the like. In some instances, these energy transfer mechanisms are relatively short range; that is, close proximity of the light harvesting multichromophore system to the signaling chromophore provides for efficient energy transfer. Under conditions for efficient energy transfer, amplification of the emission from the signaling chromophore occurs when the number of individual chromophores in the light harvesting multichromophore system is large; that is, the emission from the signaling chromophore is more intense when the incident light (the "excitation light") is at a wavelength which is absorbed by the light harvesting multichromophore system than when the signaling chromophore is directly excited by the pump light.

The multichromophore may be a conjugated polymer. Conjugated polymers (CPs) are characterized by a delocalized electronic structure and can be used as highly responsive optical reporters for chemical and biological targets. Because the effective conjugation length is substantially shorter than the length of the polymer chain, the backbone contains a large number of conjugated segments in close proximity. Thus, conjugated polymers are efficient for light harvesting and enable optical amplification via Forster energy transfer.

Polymeric dyes of interest include, but are not limited to, those dyes described by Gaylord et al. in U.S. Publication Nos. 20040142344, 20080293164, 20080064042, 20100136702, 20110256549, 20110257374, 20120028828, 20120252986, 20130190193, the disclosures of which are herein incorporated by reference in their entirety; and Gaylord et al., *J. Am. Chem. Soc.*, 2001, 123 (26), pp 6417-6418; Feng et al., *Chem. Soc. Rev.*, 2010, 39, 2411-2419; and Traina et al., *J. Am. Chem. Soc.*, 2011, 133 (32), pp 12600-12607, the disclosures of which are herein incorporated by reference in their entirety.

In some embodiments, the polymeric dye includes a conjugated polymer including a plurality of first optically active units forming a conjugated system, having a first absorption wavelength (e.g., as described herein) at which the first optically active units absorbs light to form an excited state. The conjugated polymer (CP) may be polycationic, polyanionic and/or a charge-neutral conjugated polymer.

The CPs may be water soluble for use in biological samples. Any convenient substituent groups may be included in the polymeric dyes to provide for increased water-solubility, such as a hydrophilic substituent group, e.g., a hydrophilic polymer, or a charged substituent group, e.g., groups that are positively or negatively charged in an aqueous solution, e.g., under physiological conditions. Any convenient water-soluble groups (WSGs) may be utilized in the subject light harvesting multichromophores. The term "water-soluble group" refers to a functional group that is well solvated in aqueous environments and that imparts improved water solubility to the molecules to which it is attached. In some embodiments, a WSG increases the solubility of the multichromophore in a predominantly aqueous solution (e.g., as described herein), as compared to a multichromophore which lacks the WSG. The water soluble groups may be any convenient hydrophilic group that is well solvated in aqueous environments. In some cases, the hydrophilic water soluble group is charged, e.g., positively or negatively charged. In certain cases, the hydrophilic water soluble group is a neutral hydrophilic group. In some embodiments, the WSG is a hydrophilic polymer, e.g., a polyethylene glycol, a cellulose, a chitosan, or a derivative thereof.

As used herein, the terms "polyethylene oxide", "PEO", "polyethylene glycol" and "PEG" are used interchangeably and refer to a polymer including a chain described by the formula —(CH$_2$—CH$_2$—O—)$_n$—, or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups. Functionalized PEGs that may be adapted for use in the subject multichromophores include those PEGs described by S. Zalipsky, "Functionalized poly(ethylene glycol) for preparation of biologically relevant conjugates", *Bioconjugate Chemistry* 1995, 6(2), 150-165. Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR$_3^+$, Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$^{yy}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from O, S, and NR$^{zz}$, and R$^{zz}$ and R$^{YY}$ are independently selected from H and C$_{1-3}$ alkyl.

The polymeric dye may have any convenient length. In some cases, the particular number of monomeric repeat units or segments of the polymeric dye may fall within the range of 2 to 500,000, such as 2 to 100,000, 2 to 30,000, 2 to 10,000, 2 to 3,000 or 2 to 1,000 units or segments, or such as 100 to 100,000, 200 to 100,000, or 500 to 50,000 units or segments.

The polymeric dyes may be of any convenient molecular weight (MW). In some cases, the MW of the polymeric dye may be expressed as an average molecular weight. In some instances, the polymeric dye has an average molecular weight of from 500 to 500,000, such as from 1,000 to 100,000, from 2,000 to 100,000, from 10,000 to 100,000 or even an average molecular weight of from 50,000 to 100,000. In certain embodiments, the polymeric dye has an average molecular weight of 70,000.

In certain instances, the polymeric dye includes the following structure:

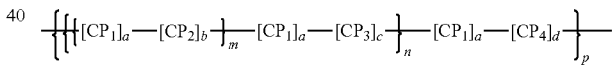

where CP$_1$, CP$_2$, CP$_3$ and CP$_4$ are independently a conjugated polymer segment or an oligomeric structure, wherein one or more of CP$_1$, CP$_2$, CP$_3$ and CP$_4$ are bandgap-lowering n-conjugated repeat units, and each n and each m are independently 0 or an integer from 1 to 10,000 and p is an integer from 1 to 100,000.

In some instances, the polymeric dye includes the following structure:

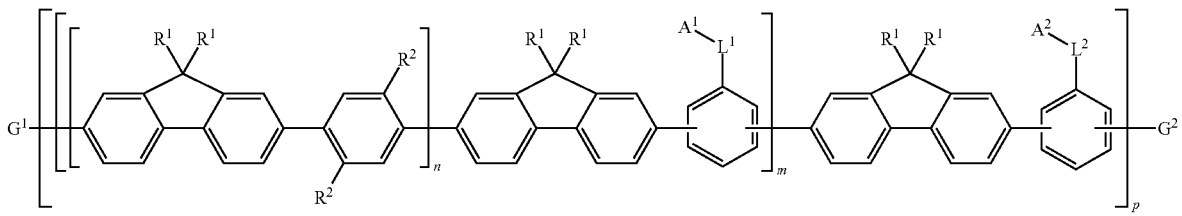

where each R$^1$ is independently a solubilizing group or a linker-dye; L$^1$ and L$^2$ are optional linkers; each R$^2$ is independently H or an aryl substituent; each A$^1$ and A$^2$ is independently H, an aryl substituent or a fluorophore; G$^1$ and $G^2$ are each independently selected from the group consisting of a terminal group, a π-conjugated segment, a linker and a linked specific binding member; each n and each m are independently 0 or an integer from 1 to 10,000; and p is an integer from 1 to 100,000. Solubilizing groups of interest include alkyl, aryl and heterocycle groups further substituted with a hydrophilic group such as a polyethylglycol (e.g., a PEG of 2-20 units), an ammonium, a sulphonium, a phosphonium, and the like.

In some cases, the polymeric dye includes, as part of the polymeric backbone, a conjugated segment having one of the following structures:

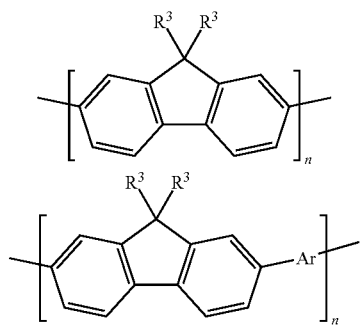

where each $R^3$ is independently an optionally substituted alkyl or aryl group; Ar is an optionally substituted aryl or heteroaryl group; and each n is an integer from 1 to 10,000. In certain embodiments, $R^3$ is an optionally substituted alkyl group. In certain embodiments, $R^3$ is an optionally substituted aryl group. In some cases, $R^3$ is substituted with a polyethyleneglycol, a dye, a chemoselective functional group or a specific binding moiety. In some cases, Ar is substituted with a polyethyleneglycol, a dye, a chemoselective functional group or a specific binding moiety.

In some instances, the polymeric dye includes the following structure:

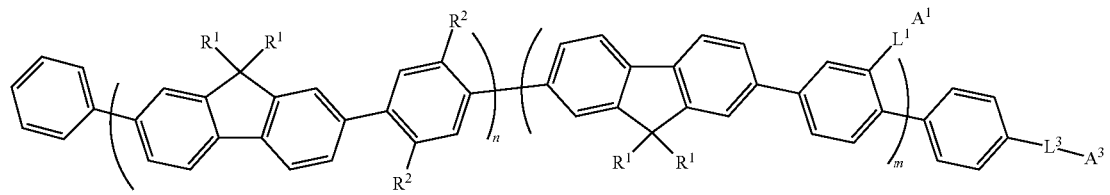

where each $R^1$ is independently a solubilizing group or a linker-dye group; each $R^2$ is independently H or an aryl substituent; each $L^1$ and $L^3$ are independently optional linkers; each $A^1$ and $A^3$ are independently H, a fluorophore, a functional group or a specific binding moiety (e.g., an antibody); and n and m are each independently 0 or an integer from 1 to 10,000, wherein n+m>1.

The polymeric dye may have one or more desirable spectroscopic properties, such as a particular absorption maximum wavelength, a particular emission maximum wavelength, extinction coefficient, quantum yield, and the like (see e.g., Chattopadhyay et al., "Brilliant violet fluorophores: A new class of ultrabright fluorescent compounds for immunofluorescence experiments." *Cytometry Part A*, 81A (6), 456-466, 2012).

In some embodiments, the polymeric dye has an absorption curve between 280 nm and 475 nm. In certain embodiments, the polymeric dye has an absorption maximum (excitation maximum) in the range 280 nm and 475 nm. In some embodiments, the polymeric dye absorbs incident light having a wavelength in the range between 280 nm and 475 nm.

In some embodiments, the polymeric dye has an emission maximum wavelength ranging from 400 nm to 850 nm, such as 415 nm to 800 nm, where specific examples of emission maxima of interest include, but are not limited to: 421 nm, 510 nm, 570 nm, 602 nm, 650 nm, 711 nm and 786 nm. In some instances, the polymeric dye has an emission maximum wavelength in a range selected from the group consisting of 410 nm to 430 nm, 500 nm to 520 nm, 560 nm to 580 nm, 590 nm to 610 nm, 640 nm to 660 nm, 700 nm to 720 nm, and 775 nm to 795 nm. In certain embodiments, the polymeric dye has an emission maximum wavelength of 421 nm. In some instances, the polymeric dye has an emission maximum wavelength of 510 nm. In some cases, the polymeric dye has an emission maximum wavelength of 570 nm. In certain embodiments, the polymeric dye has an emission maximum wavelength of 602 nm. In some instances, the polymeric dye has an emission maximum wavelength of 650 nm. In certain cases, the polymeric dye has an emission maximum wavelength of 711 nm. In some embodiments, the polymeric dye has an emission maximum wavelength of 786 nm. In certain instances, the polymeric dye has an emission maximum wavelength of 421 nm±5 nm. In some embodiments, the polymeric dye has an emission maximum wavelength of 510 nm±5 nm. In certain instances, the polymeric dye has an emission maximum wavelength of 570 nm±5 nm. In some instances, the polymeric dye has an emission maximum wavelength of 602 nm±5 nm. In some embodiments, the polymeric dye has an emission maximum wavelength of 650 nm±5 nm. In certain instances, the polymeric dye has an emission maximum wavelength of 711 nm±5 nm. In some cases, the polymeric dye has an emission maximum wavelength of 786 nm±5 nm. In certain embodiments, the polymeric dye has an emission maximum selected from the group consisting of 421 nm, 510 nm, 570 nm, 602 nm, 650 nm, 711 nm and 786 nm.

In some instances, the polymeric dye has an extinction coefficient of $1\times10^6$ cm$^{-1}$M$^{-1}$ or more, such as $2\times10^6$ m or more, $2.5\times10^6$ cm$^{-1}$M$^{-1}$ or more, $3\times10^6$ cm$^{-1}$M$^{-1}$ or more, $4\times10^6$ cm$^{-1}$M$^{-1}$ or more, $5\times10^6$ cm$^{-1}$M$^{-1}$ or more, $6\times10^6$ cm$^{-1}$M$^{-1}$ or more, $7\times10^6$ cm$^{-1}$M$^{-1}$ or more, or $8\times10^6$ cm$^{-1}$M$^{-1}$ or more. In certain embodiments, the polymeric dye has a quantum yield of 0.05 or more, such as 0.1 or more, 0.15 or more, 0.2 or more, 0.25 or more, 0.3 or more, 0.35 or more, 0.4 or more, 0.45 or more, 0.5 or more, or even more. In certain cases, the polymeric dye has a quantum yield of 0.1 or more. In certain cases, the polymeric dye has a quantum yield of 0.3 or more. In certain cases, the polymeric dye has a quantum yield of 0.5 or more. In some embodiments, the polymeric dye has an extinction coefficient of $1\times10^6$ or more and a quantum yield of 0.3 or more.

In some embodiments, the polymeric dye has an extinction coefficient of $2\times10^6$ or more and a quantum yield of 0.5 or more.

In certain embodiments, the dried dye composition includes other types of dye compositions, such as one or more non-polymeric dye compositions. As discussed above, dyes may include detectable moieties or markers that are detectible based on, for example, fluorescence emission maxima, fluorescence polarization, fluorescence lifetime, light scatter, mass, molecular mass, or combinations thereof. In certain embodiments, the non-polymeric dye includes a fluorophore (i.e., a fluorescent label, fluorescent dye, etc.). Fluorophores of interest may include but are not limited to dyes suitable for use in analytical applications (e.g., flow cytometry, imaging, etc.). A large number of non-polymeric dyes are commercially available from a variety of sources, such as, for example, Molecular Probes (Eugene, Oreg.) and Exciton (Dayton, Ohio). For example, the fluorophore of the non-polymeric dye may be 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy3.5, Cy5, Cy5.5, and Cy7; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin (PE); o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; carotenoid-protein complexes, such as peridinin-chlorophyll proteins (PerCP); allophycocyanin (APC); or combinations thereof.

In some instances, the dye component of a given dried dye composition is a conjugate of a dye moiety and a specific binding member. The specific binding member and the dye moiety can be conjugated (e.g., covalently linked) to each other at any convenient locations of the two molecules, via an optional linker.

As used herein, the term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules. Thus the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-5}$ M or less, e.g., $10^{-9}$ M or less, $10^{-19}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10\times10^{-9}$ M or less, such as $1\times10^{-9}$ M or less, $3\times10^{-10}$ M or less, $1\times10^{-10}$ M or less, $3\times10^{-11}$ M or less, $1\times10^{-11}$ M or less, $3\times10^{-12}$ M or less or $1\times10^{-12}$ M or less.

The specific binding member can be proteinaceous. As used herein, the term "proteinaceous" refers to a moiety that is composed of amino acid residues.

A proteinaceous moiety can be a polypeptide. In certain cases, the proteinaceous specific binding member is an antibody. In certain embodiments, the proteinaceous specific binding member is an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. The term antibody is meant to include full length antibodies and may refer to a natural antibody from any organism, an engineered antibody, or an antibody generated recombinantly for experimental, therapeutic, or other purposes as further defined below.

Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is a Fab fragment, a F(ab')$_2$ fragment, a scFv, a diabody or a triabody. In certain embodiments, the specific binding member is an antibody. In some cases, the specific binding member is a murine antibody or binding fragment thereof. In certain instances, the specific binding member is a recombinant antibody or binding fragment thereof.

In certain embodiments, the dye compositions included in the dried dye reagent device include polymeric dye compositions, as described above. In some cases, the dye compositions included in the dried dye reagent device include non-polymeric dye compositions, as described above. In some instances, the dye compositions included in the dried dye reagent device include both polymeric dye compositions and non-polymeric dye compositions. As described above, the dried dye reagent devices may include a plurality of dye compositions as described above, which dye compositions may be identical or distinct. For example, the devices may include two or more, such as three or more, distinct dried polymeric dye compositions and two or more, such as three or more, or four or more, or five or more, distinct non-polymeric dye compositions. In some cases, the device includes three or more distinct polymeric dye compositions and five or more distinct non-polymeric dye compositions.

As described above, the dye device may include both a polymeric dye composition and a non-polymeric dye composition. In some instances, a polymeric dye composition is mixed with a non-polymeric dye composition. In certain embodiments, the mixture of the polymeric dye composition and the non-polymeric dye composition do not undergo significant dye-dye interactions between the polymeric dye composition and the non-polymeric dye composition. For instance, the fluorescence emission energy of the polymeric dye composition is not significantly quenched by interactions with the non-polymeric dye composition. In some cases, the fluorescence emission energy of the polymeric dye composition is not significantly dissipated by a non-radiative transition. In these embodiments, the detectable fluorescence of the polymeric dye composition is not significantly less than would be expected as compared to the fluorescence of the polymeric dye composition in the absence of the non-polymeric dye composition. Similarly, in some embodiments, the fluorescence emission energy of the non-polymeric dye composition is not significantly quenched by interactions with the polymeric dye composition. For instance, the fluorescence emission energy of the non-polymeric dye composition may not be significantly dissipated by a non-radiative transition. In these embodiments, the detectable fluorescence of the non-polymeric dye composition is not significantly less than would be expected as compared to the fluorescence of the non-polymeric dye composition in the absence of the polymeric dye composition. In such instances, the polymeric and non-polymeric dyes of the mixed composition are stably associated with the same high surface area solid support, such that in these instances a given high surface area solid support includes two or more, such as three or more, including four or more different dyes, where in some instances only one of the dyes is a polymeric dye.

In certain embodiments, the dye composition includes a dye, such as a polymeric and/or non-polymeric dye, as described above. The dye composition may also include other components, such as, but not limited to a solvent, a buffer, a stabilizer, and the like. For example, the dye composition may include a stabilizer that reduces and/or substantially prevents degradation of the dye in the dye composition. In some cases, the presence of a stabilizer in the dye composition is sufficient to reduce and/or substantially prevent degradation of the dye in the dye composition for a certain period of time, such as 24 hours or more, or 48 hours or more, or 72 hours or more, or 4 days or more, or 5 days or more, or 6 days or more, or 1 week or more, or 2 weeks or more, or 3 weeks or more, or 4 weeks or more, or 2 months or more, or 3 months or more, or 4 months or more, or 5 months or more, or 6 months or more, or 9 months or more, or 1 year or more. Examples of stabilizers include, but are not limited to, bovine serum albumin (BSA), sodium azide, glycerol, phenylmethanesulfonyl fluoride (PMSF), and the like. Additional additives may also be present in the composition, such as, additives that preserve cells present in whole blood, e.g., platelet stabilizing factor, and the like. Examples of additives that may be included in the composition are anticoagulants such as ethylenediaminetetraacetic acid (EDTA), buffered citrate, heparin, and the like. The composition may include these additives in a liquid or dried state.

Among the dried dye compositions in a given container, the dye compositions may be homogenous with respect to the nature of the high surface area solid support (i.e., the high surface area solid support component may be the same among the different dye compositions), or the dried dye compositions may be heterogeneous with respect to the nature of the high surface area solid support (i.e., the high surface area solid support component may be the different among at least two of the different dye compositions). Where the dried dye compositions are heterogeneous with respect to the solid support, in some instances, all of the distinct dried dye compositions have a different or distinct solid support, where any two solid supports are considered to be distinct if they differ from each other in terms of at least one of physical characteristic (e.g., shape, surface area, porosity, color) and/or material.

In certain embodiments, the reagent device also includes a calibration standard. The calibration standard may be useful for determining the accuracy of the assay and for ensuring consistency between subsequent assays. In some cases, the calibration standard includes a labelled bead, such as a fluorescently labelled bead. The fluorescently labelled bead may be a standard fluorescently labeled bead that is typically used as a calibration standard. Examples of standard fluorescently labeled beads include, but are not limited to, fluorescently labelled microparticles or nanoparticles. In some cases, the fluorescently labeled beads are configured such that they remain suspended in the assay mixture and do not substantially settle or aggregate. In some embodiments, the fluorescently labeled beads include, but are not limited to, fluorescently labelled polystyrene beads, fluorescein beads, rhodamine beads, and other beads tagged with a fluorescent dye. Additional examples of fluorescently labeled beads are described in U.S. Pat. Nos. 6,350,619; 7,738,094; and 8,248,597, the disclosures of each of which are herein incorporated by reference in their entirety.

In some instances, the one or more dried dye compositions are retained at a location of the container by a retainer, i.e., the dye compositions are stably associated with a given location or region of the container, e.g., a given location on the inner surface of the container. Any convenient retainer may be employed. In some instances the retainer is a mesh, where the mesh size may vary, ranging in some instances from 0.5 mm to 5 mm. The retainer may be fabricated from any suitable material, where materials of interest include, but are not limited to: glass materials (e.g., silicates), ceramic materials (e.g., calcium phosphates), metallic materials, and polymeric materials, etc. such as for example, polyethylene, polypropylene, polytetrafluoroethylene, polyvinylidine fluoride, and the like.

In some cases, the dried dye reagent devices facilitate storage of the dye compositions for an extended period of time. For instance, a dried dye reagent device may be a storage stable device. In some cases, the dye compositions contained in the device are storage stable dye compositions, where the dye compositions are substantially stable for an extended period of time. By "stable" or "storage stable" or "substantially stable" is meant a dye composition that does not significantly degrade and/or lose activity over an extended period of time. For example, a storage stable dye composition may not have significant loss of fluorescence activity due to degradation of the dye composition over an extended period of time, such as 10% or less loss of fluorescence activity, or 9% or less, or 8% or less, or 7% or less, or 6% or less, or 5% or less, or 4% or less, or 3% or less, or 2% or less, or 1')/0 or less loss of fluorescence activity over an extended period of time. In certain instances, a storage stable dye composition has 5% or less loss of fluorescence activity over an extended period of time. In some cases, a storage stable dye composition substantially retains its fluorescence activity over an extended period of time, such as retains 100% of its activity, or 99% or more, or 98% or more, or 97% or more, or 96% or more, or 95% or more, or 94% or more, or 93% or more, or 92% or more, or 91% or more, or 90% or more, or 85% or more, or 80% or more, or 75% or more of its activity over an extended period of time. For example, a storage stable dye composition may retain 90% or more of its fluorescence activity over an extended period of time. In some cases, a storage stable composition retains 95% or more of its fluorescence activity over an extended period of time. An extended period of time is a period of time such as 1 week or more, or 2 weeks or more, or 3 weeks or more, or 1 month or more, or 2 months or more, or 3 months or more, or 4 months or more, or 6 months or more, or 9 months or more, or 1 year or more, or 1.5 years (e.g., 18 months) or more, or 2 years or more, or 2.5 years (e.g., 30 months) or more, or 3 years or more, or 3.5 years (e.g., 42 months) or more, or 4 years or more, or 4.5 years (e.g., 54 months) or more, or 5 years or more. For instance, an extended period of time may be 6 months or more. In some cases, an extended period of time is 9 months or more. In some cases, an extended period of time is 1 year (e.g., 12 months) or more. In some cases, an extended period of time is 1.5 years (e.g., 18 months) or more. In some cases, an extended period of time is 2 years (e.g., 24 months) or more. In some instances, the extended period of time is 10 years or less, such as 7.5 years or less, including 5 years or less, e.g., 2 years or less.

An example of a dried dye reagent device according to embodiments of the present disclosure is shown in FIG. 1. The reagent device shown in FIG. 1 is an embodiment of a multiplex dye device. In FIG. 1, the reagent device 10 is configured as a vial or test tube; e.g., the reagent device 10 includes a container 12 in the form of a vial (test tube). The reagent device 10 includes three different dried polymeric dye compositions (14, 16, 18), where each dye composition includes a polymeric dye stably associated with high surface area solid support in the form of a porous frit. Also shown is metal retainer in the form of a metal mesh 19 which is positioned in the container 12 to retain the dye compositions at the bottom of the container.

Figure 3:
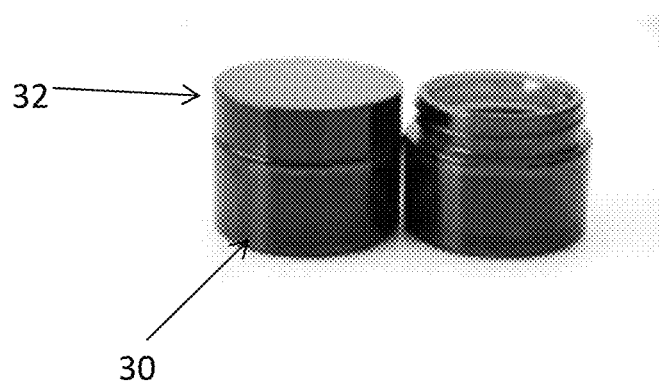
FIG. 3 provides an illustration of a dried reagent device according to an embodiment of the invention.

FIG. 3 provides a depiction of another embodiment of a reagent device. In FIG. 3, the device includes a container 30 in the form of an amber colored glass bottle with a removable cap 32. The bottle includes between 2 and 100 identical dried reagent compositions made up of a dye stably associate with a porous frit. The dried reagent compositions are not stably associated with any surface, such as any location of the inner wall, of the bottle. As such, the move freely relative to the inner walls of the bottle.

Figure 4:
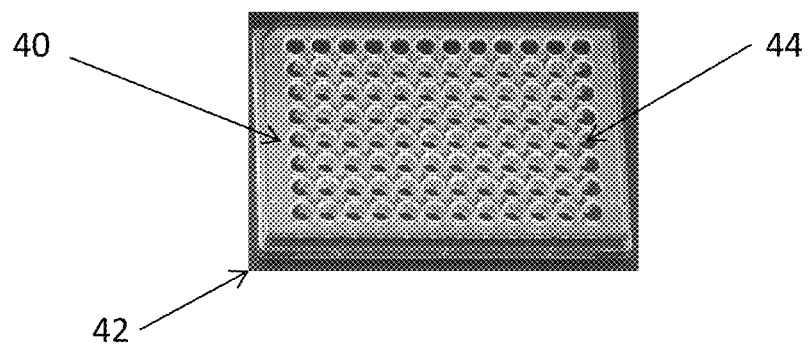
FIG. 4 provides an illustration of a dried reagent device according to an embodiment of the invention.

FIG. 4 provides a depiction of another embodiment of a reagent device. In FIG. 4, the device is a 96-well mesh plate 40 that is operatively coupled to 96-well tray 42. In each well is a dried reagent composition 44 made up of a dye stably associated with a porous frit.

Methods of Use

Aspects of the present disclosure also include methods of using the subject dried dye reagent devices. As described above, a dried dye reagent device of the invention may include a container and one or more dried dye compositions (e.g., multiple identical dried dye compositions, first and second polymeric dye compositions, etc.), each having a dye stably associated with a high surface area solid support. In some instances, the method of using the reagent device includes reconstituting the dye composition. In certain embodiments, the method includes combining a volume of a liquid and the device in a manner sufficient to produce a reconstituted dye composition. The volume of liquid may be added to the device using any convenient liquid handling apparatus, such as, but not limited to, syringes, needles, pipets, aspirators, among other liquid handling devices. The combining step of the method may include positioning the volume of liquid inside the liquid container. By positioning the volume of liquid inside the liquid container, the liquid may contact the dried polymeric dye compositions in the liquid container. In some cases, the liquid (e.g., water) may be absorbed by the dried dye compositions, thus reconstituting the dried dye compositions.

In certain embodiments, the liquid includes a biological sample. In some cases, the biological sample may be derived from specific biological fluids, such as, but not limited to, blood, mucus, lymphatic fluid, synovial fluid, cerebrospinal fluid, saliva, bronchoalveolar lavage, amniotic fluid, amniotic cord blood, urine, vaginal fluid and semen. In some embodiments, the biological sample includes whole blood or a fraction thereof. In some embodiments, the biological sample includes blood plasma.

In certain embodiments, the device is a sealed device, such as where the device includes a seal (e.g., a water-tight and/or air-tight seal). In these instances, the method may include removing the seal prior to positioning the volume of liquid inside the liquid container. Removing the seal on the device may expose the contents of the liquid container to the surrounding environment and allow access to the interior volume of the liquid container. Thus, a user that has access to the interior volume of the liquid container may position the volume of liquid inside the liquid container for reconstitution of the dried dye compositions inside the liquid container.

In certain embodiments, the method also includes mixing the contents of the liquid container after positioning the volume of liquid inside the liquid container. The mixing may be performed using any convenient protocol. For example, the mixing may be performed using an agitator. The agitator may be any convenient agitator sufficient for mixing the liquid inside the liquid container, including, but not limited to, vortexers, sonicators, shakers (e.g., manual, mechanical, or electrically powered shakers), rockers, oscillating plates, magnetic stirrers, static mixers, rotators, blenders, mixers, tumblers, orbital shakers, among other agitating protocols.

Where desired, the liquid reconstituted dye composition may be separated from the high surface area component. In such instances, separation may be achieved using any convenient protocol. The high surface area component may be removed the reconstituted dye composition using a convenience instrument, such as a tweezer. Alternatively, e.g., in embodiments where the high surface area component is retained by a retaining structure, the reconstituted dye composition may be removed from the container, e.g., by pouring it from the container, aspirating it from the container, etc. In those embodiments such as illustrated in FIG. 4 where the dried dye composition is in positioned in a mesh well operatively coupled to receiving plate, the mesh plate that includes the mesh well may be separated from the receiving plate, leaving the reconstituted dye composition for subsequent use.

In some cases, the method also includes assaying the reconstituted dye composition. In such instances, the methods may include removing an amount or volume of the reconstituted dye composition from the container, e.g., for assaying. Assaying the reconstituted dye composition may be performed using any suitable assay apparatus. For example, the assay apparatus may be a flow cytometer. In these embodiments, the assaying includes flow cytometrically analyzing the reconstituted dye composition. In some instances, the assaying includes contacting the reconstituted dye composition with electromagnetic radiation (e.g., light), such as electromagnetic radiation having a wavelength that corresponds to the excitation maxima of the reconstituted dye composition. The assaying may further include detecting emitted light from the excited dye compositions. For instance, the method may include detecting emitted light from the excited dye compositions at one or more wavelengths that correspond to the emission maxima of the dye compositions.

Suitable flow cytometry systems and methods for analyzing samples that may be employed in methods of the invention include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem*. January; 49(pt 1):17-28; Linden, et. al., *Semin Throm Hemost*. 2004 October; 30(5):502-11; Alison, et al. *J Pathol*, 2010 December; 222(4):335-344; and Herbig, et al. (2007) *Crit Rev Ther Drug Carrier Syst*. 24(3):203-255; the disclosures of which are incorporated herein by reference. In certain instances, flow cytometry systems of interest include BD Biosciences FACSCanto™ and FACSCanto II™ flow cytometers, BD Biosciences FACSVantage™, BD Biosciences FACSort™, BD Biosciences FACSCount™, BD Biosciences FACScan™, and BD Biosciences FACSCalibur™ systems, BD Biosciences Influx™ cell sorter, BD Biosciences Accuri™ C6 flow cytometer; BD Biosciences LSRFortessa™ flow cytometer, BD Biosciences LSRFortessa™ X-20 flow cytometer, BD Biosciences FACSVerse™ flow cytometer, BD Biosciences FACSAria™ III and BD FACSAria™ Fusion flow cytometers, BD Biosciences FACSJazz™ flow cytometer, or the like. In certain embodiments, the subject systems are flow cytometric systems, such as those described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosure of which are herein incorporated by reference in their entirety.

Other methods of analysis may also be used, such as, but not limited to, liquid chromatography-mass spectrometry or gas chromatography-mass spectrometry systems. For example, assaying may include the use of an analytical separation device such as a liquid chromatograph (LC), including a high performance liquid chromatograph (HPLC), a micro- or nano-liquid chromatograph or an ultra-high pressure liquid chromatograph (UHPLC) device, a capillary electrophoresis (CE), or a capillary electrophoresis chromatograph (CEC) apparatus. Mass spectrometer (MS) systems may also be used to assay the dye compositions. Examples of mass spectrometers may include, but are not limited to, electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof.

In certain embodiments, the device is included in an apparatus that is fully automated. By "fully automated" is meant that the apparatus receives a reagent device and prepares a reconstituted dye composition with little to no human intervention or manual input into the subject systems. In certain embodiments, the subject systems are configured to prepare and analyze the reconstituted dye composition without any human intervention.

In certain embodiments, the method also includes storing the reconstituted dye composition for a period of time. The reconstituted dye composition may be stored for a period of time before, during and/or after assaying the reconstituted dye composition. In some instances, the reconstituted dye composition is stored for a period of time such as 24 hours or more, or 48 hours or more, or 72 hours or more, or 4 days or more, or 5 days or more, or 6 days or more, or 1 week or more, or 2 weeks or more, or 3 weeks or more, or 4 weeks or more, or 2 months or more, or 3 months or more, or 4 months or more, or 5 months or more, or 6 months or more, or 9 months or more, or 1 year or more. In certain cases, the reconstituted dye composition is stored for 24 hours or more. In certain cases, the reconstituted dye composition is stored for 48 hours or more. In certain cases, the reconstituted dye composition is stored for 72 hours or more. In certain cases, the reconstituted dye composition is stored for 1 week or more. In certain cases, the reconstituted dye composition is stored for 2 weeks or more. In certain cases, the reconstituted dye composition is stored for 3 weeks or more.

Embodiments of the method may further include shipping the reconstituted dye composition to a remote location. A "remote location," is a location other than the location at which the dye composition is reconstituted. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or one hundred miles or more apart.

Where the reagent device is configured for storing dried dye compositions, e.g., as depicted in FIG. 3, methods may include removing one or more dried reagent compositions from the container. A dried reagent composition may be removed from a container using any convenient protocol, e.g., by hand or with a suitable instrument, such as a tweezer, including a manual tweezer or a vacuum tweezer. The removed dried dye composition may be placed in a suitable receptacle, e.g., a well of a multi-well plate or a vial, such as described above, and combined with a liquid to reconstitute the dye, such as described above.

Methods of Making

Aspects of the present disclosure also include methods of making a dried dye reagent device as described herein. In certain embodiments, the methods of making include positioning one or more dried dye compositions, where each dried dye composition includes one or more dyes stably associated with a high surface area solid support, into a container. For example, the methods of making may include positioning one or more dried dye compositions (e.g., first and second dried dye compositions) into a container, e.g., at the bottom of a vial or well, in a bottle, in a dispenser, etc. The dried dye compositions may be positioned in the container using any convenient protocol, such as, but not limited to, any convenient manual or automated deposition protocol, e.g., dropping the compositions into the container, using a placement device to position the composition in the container, etc.

After positioning the dye compositions in the container (e.g., liquid container), the methods may include positioning a retaining member in container in a manner sufficient to retain the dye compositions at a location in the container. The retaining member, e.g., as described above, may be positioned in the container using any convenient protocol, such as, but not limited to, any convenient manual or automated deposition protocol, e.g., manually positions in the retaining member into the container, using a placement device to position the retaining member in the container, etc.

In some instances, the methods may further include sealing the container that contains the two or more distinct dried dye compositions. For example, the method may include applying a seal to the liquid container. As described above, the seal may be a water-tight and/or an air-tight seal. In some instances, the seal is a removable or a breakable seal, which allows a user to subsequently gain access to the contents of the container.

As described above, the devices may also include a calibration standard, such as standard fluorescently labelled beads. In these embodiments, the methods may further include positioning a set of standard fluorescently labelled beads in the container. The positioning may be performed using any convenient technique for handling beads. For example, the beads may be provided in a liquid, such as a suspension of beads in a liquid. In these instances, the liquid containing the beads may be positioned in the container using any convenient liquid handling apparatus, such as, but not limited to, syringes, needles, pipets, aspirators, among other liquid handling devices. In some instances, the liquid containing the beads may be positioned on the surface of the solid support using a printer, such as, but not limited to, an inkjet printer. In these instances, the beads may be positioned and then dried in the container, prior to introduction of the dried dye compositions.

Figure 2:
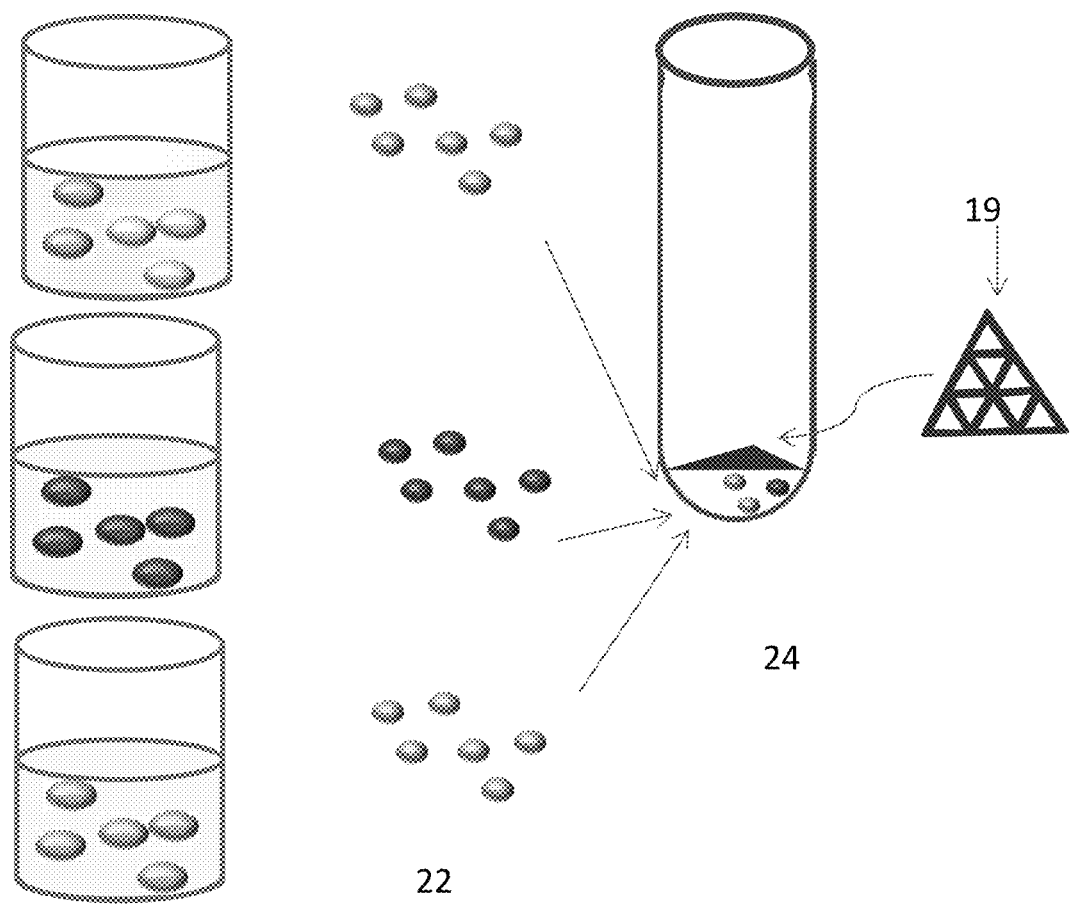
FIG. 2 provides an illustration of a fabrication protocol that may be employed to produce a device as shown in FIG. 1.

FIG. 2 provides an illustration of a fabrication protocol for the device illustrated in FIG. 1. In FIG. 2, three different dried polymeric dye compositions are prepared in step 20 by soaking porous frits in aqueous solutions of three different polymeric dye/antibody conjugates. Next, in step 22 the different frits are dried, e.g., by freeze drying, to produce dried dye compositions. Next, in step 24, a dried dye composition from each of the three result populations is placed into a tube, and a metal mesh 19 is positioned over the dried compositions to retain the compositions in the tube, e.g., during packaging.

Kits

Aspects of the disclosure also include kits that include a dried dye reagent device as described herein. In certain embodiments, the kit includes a subject device and a packaging configured to hold the reagent device. The packaging may be a sealed packaging, e.g., a water vapor-resistant container, optionally under an air-tight and/or vacuum seal. In certain instances, the packaging is a sterile packaging, configured to maintain the device enclosed in the packaging in a sterile environment. By "sterile" is meant that there are substantially no microbes (such as fungi, bacteria, viruses, spore forms, etc.). The kits may further include a buffer. For instance, the kit may include a buffer, such as a sample buffer, a wash buffer, an assay buffer, and the like. The kits may further include additional reagents, such as but not limited to, detectable labels (e.g., fluorescent labels, colorimetric labels, chemiluminescent labels, multicolor reagents, avidin-streptavidin associated detection reagents, radiolabels, gold particles, magnetic labels, etc.), and the like. In certain embodiments, the kits may also include a calibration standard. For example, the kits may include a set of labelled beads, such as a set of standard fluorescently labelled beads. In some instances the kits may include a dried dye composition handling instrument, e.g., a tweezer.

Figure 5:
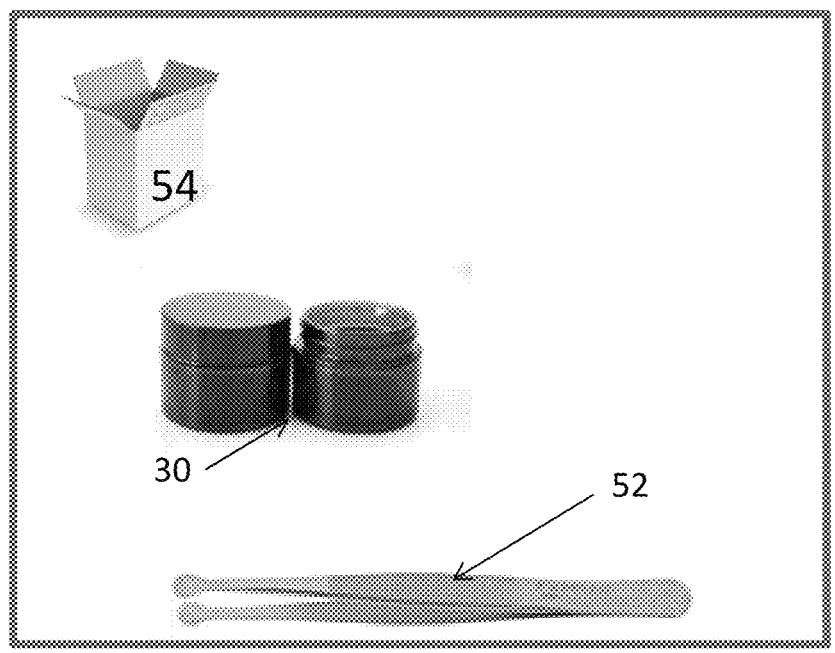
FIG. 5 provides an illustration of a kit including the reagent device as shown in FIG. 3, according to an embodiment of the invention.
Figure 6:
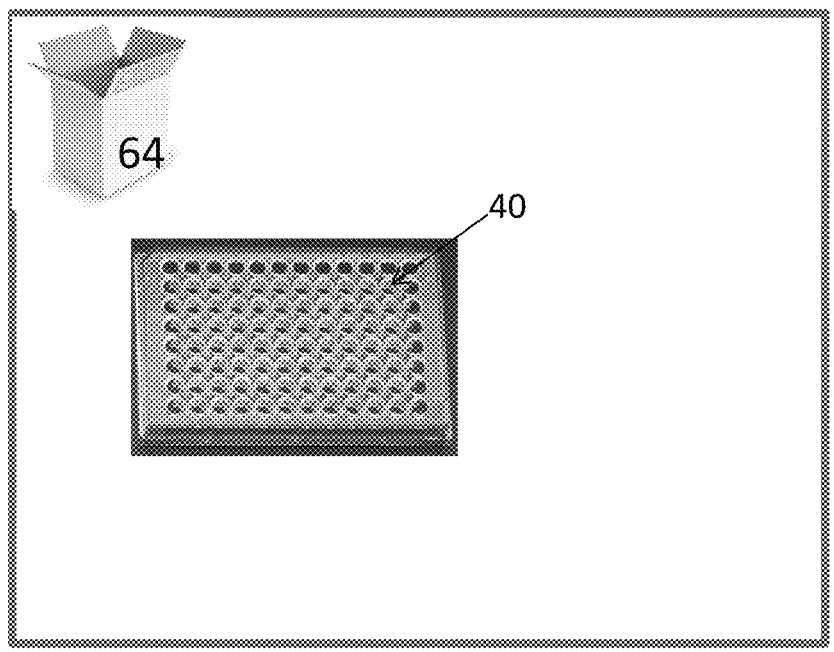
FIG. 6 provides an illustration of a kit including the reagent device as shown in FIG. 4, according to an embodiment of the invention.

FIG. 5 provides an illustration of a kit that includes the reagent device illustrated in FIG. 3. In the kit, in addition to the device 30, also present is a tweezer 52 and a box 54 (i.e., packaging). FIG. 5 provides an illustration of a kit that includes the reagent device illustrated in FIG. 4. In the kit, in addition to the device 40 that includes a 96 well plate with mesh insert having dried dye reagent discs placed in the insert, also present is a box 64 (i.e., packaging).

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory (e.g., flash memory), etc., on which the information has been recorded or stored. Yet another form that may be present is a website address which may be used via the Internet to access the information at a removed site. Any convenient form of instructions may be present in the kits.

Utility

The subject devices and methods find use in applications where cell analysis from a biological sample may be desired for research, laboratory testing or for use in therapy. In some embodiments, the subject devices and methods facilitate analysis of cells obtained from fluidic or tissue samples such as specimens for diseases, including but not limited to cancer. Devices and methods of the present disclosure also allow for analyzing cells from a biological sample (e.g., organ, tissue, tissue fragment, fluid) with enhanced efficiency and low cost.

The subject devices and methods find use in applications where the analysis of a sample using two or more dye compositions is desired. For example, the subject devices and methods find use in applications where the analysis of a sample using two or more dye compositions is desired, such as two or more polymeric dye compositions. Embodiments of the subject devices and methods also find use in applications where analysis of a sample using two or more polymeric dye compositions in combination with one or more non-polymeric dye compositions is desired. Thus, the subject devices and methods find use in applications where a sample is analyzed for two or more analytes of interest using two or more corresponding dye compositions. In some cases, where non-polymeric dye compositions are also included in the reagent devices, the subject devices and methods find use in applications where a sample is analyzed for two or more analytes of interest using two or more corresponding polymeric dye compositions and non-polymeric dye compositions.

The subject reagent devices and methods find use in applications where a minimization in dye-dye interactions is desired. As described herein, the subject reagent devices and methods provide two or more distinct dried polymeric dye compositions, where each dye composition includes a dye stably associated with high surface area solid support, facilitating a minimization in dye-dye interactions. A minimization in dye-dye interactions may facilitate the collection of more precise and/or accurate data with respect to the assays performed using the subject reagent devices. For instance, the subject reagent devices and methods may facilitate a reduction in dye-dye interactions as compared to reagent devices in which two or more dye compositions are provided but are not stably associated with different high surface area solid supports.

The devices and methods described herein find use in application where a panel of analytes in sample is to be assayed. Where desired, the devices and methods may be used in customized panel assays, where a user may specify the analytes of a panel of interest and reagent device with dyes selected for the panel prepare on a custom bases. The dyes of the panel may be present in separate dried dye compositions, or two or more of the dyes for the panel may be combined in a single dried dye composition, e.g., as described above.

As can be appreciated from the disclosure provided above, embodiments of the present disclosure have a wide variety of applications. Accordingly, the examples presented herein are offered for illustration purposes and are not intended to be construed as a limitation on the embodiments of the present disclosure in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

I. Materials and Methods
A. Multiplex Dye Device Preparation

Plasma etched polyethylene frits are placed into wells of a 96-well plate, one per well. 5 µL of reagent composition that includes a single dye/antibody conjugate or 10× bovine serum albumin is added to each well. Four different reagent compositions are employed, i.e., CD4-BV510, CD3-BV421, CD7-BV605, CD45-FITC. (BV and FITC available from BD Biosciences, San Jose, Calif.). The resultant plate is dried at 27° C. overnight or 37° C. for 1 hour. Following drying, each of the five types of resultant conjugate discs is combined in a 12×75 mm test tube, foil covered and put in a pouch.

B. Combination of Reagents Discs with a Sample

100 µL whole blood is combined with 1 µL 1% PEG 550 and mixed. The resultant PEG/blood mixture is then introduced into the tube prepared in IA, above, and vortexed for 20 seconds (2 times of 10 seconds mixing). The resultant mixture is incubated for 30 min, followed by lysing with 1×FACSLyse (BD Biosciences, San Jose, Calif.). The resultant cell lysate is transferred to a new tube the reagent discs are discarded. Cells are pelleted by centrifugation, the FACSLyse aspirated. Cells are then washed using wash buffer (PBS+0.5% BSA+0.1% NaN3). The cells are then pelleted by centrifugation, and resuspended in wash buffer for acquisition and analysis on flow cytometer.

Notwithstanding the appended clauses, the disclosure set forth herein is also defined by the following clauses:

1. A method comprising:
   positioning a volume of a liquid into a container comprising a first dried dye composition comprising one or more dyes stably associated with a first high surface area solid support to produce a reconstituted dye composition in the container; and
   removing the reconstituted dye composition from the container.
2. The method according to Clause 1, wherein the first dried dye composition comprises a single dye.
3. The method according to Clause 1, wherein the first dried dye composition comprises two or more dyes.
4. The method according to any of Clauses 1 to 3, wherein the container further comprises a second dried dye composition comprising a second dye stably associated with a second high surface area solid support.
5. The method according to Clause 4, wherein the second dried dye composition comprises a single dye.
6. The method according to Clause 4, wherein the second dried dye composition comprises two or more dyes.
7. The method according to any of the preceding clauses, wherein the liquid comprises a biological sample.
8. The method according to Clause 7, wherein the biological sample comprises whole blood or a fraction thereof.
9. The method according to any of Clauses 1 to 8, wherein the method further comprises assaying the reconstituted dye composition.
10. The method according to Clause 9, wherein the assaying comprises flow cytometrically analyzing the reconstituted dye composition.

11. A reagent device comprising:
a container; and
distinct first and second dried dye compositions present in the container, wherein:
the first dried dye composition comprises a first dye stably associated with a first high surface area solid support; and
the second dried dye composition comprises a second dye stably associated with a second high surface area solid support.

12. The device according to Clause 11, wherein the first and second dyes differ from each other by at least one of excitation maxima and emission maxima.

13. The device according to Clauses 11 or 12, wherein the first and second dyes are first and second polymeric dyes.

14. The device according to Clause 13, wherein the first and second polymeric dyes are water soluble conjugated polymers.

15. The device according to any of Clauses 11 to 14, wherein the first and second dyes are conjugates of a dye moiety and a specific binding member.

16. The device according to Clause 15, wherein the specific binding member comprises an antibody or binding fragment thereof.

17. The device according to any of Clauses 11 to 16, wherein the first and second high surface area solid supports have a surface area that is 0.5 $mm^2$ or more.

18. The device according to any of Clauses 11 to 17, wherein the first and second high surface area solid supports have a longest dimension ranging from 1 to 5 mm.

19. The device according to any of Clauses 11 to 18, wherein the first and second high surface area solid supports are porous.

20. The device according to Clause 19, wherein the first and second high surface area solid supports have a porosity ranging from 5μ to 90μ.

21. The device according to any of Clauses 11 to 20, wherein the first and second high surface area solid supports are fabricated from an inert material.

22. The device according to Clause 21, wherein the inert material is selected from a plastic, a glass and a ceramic.

23. The device according to Clause 22, wherein the inert material is a plastic.

24. The device according to any of Clauses 11 to 23, wherein the device comprises three or more distinct dried dye compositions each comprising a dye stably associated with a high surface area solid support.

25. The device according to any of Clauses 11 to 24, wherein the container is configured to hold a volume ranging from 0.1 ml to 250 ml.

26. The device according to Clause 25, wherein the container is a vial.

27. The device according to Clause 25, wherein the container is a well of a multi-well plate.

28. The device according to any of Clauses 11 to 27, wherein the container is sealed.

29. The device according to any of Clauses 11 to 28, wherein distinct first and second dried dye compositions are retained at a location of the container by a retainer.

30. The device according to Clause 29, wherein the retainer comprises a metal retainer.

31. A method comprising:
positioning a volume of a liquid into a reagent device comprising:
a container; and
distinct first and second dried dye compositions present in the container, wherein:
the first dried dye composition comprises a first dye stably associated with a first high surface area solid support; and
the second dried dye composition comprises a second dye stably associated with a second high surface area solid support;
to produce a reconstituted dye mixture in the container.

32. The method according to Clause 31, wherein the liquid comprises a biological sample.

33. The method according to Clause 32, wherein the biological sample comprises whole blood or a fraction thereof.

34. The method according to any of Clauses 31 to 33, wherein the first and second dyes differ from each by at least one of excitation and emission maxima.

35. The method according to any of Clauses 31 to 34, wherein the first and second dyes are first and second polymeric dyes.

36. The method according to Clause 35, wherein the first and second polymeric dyes are water soluble conjugated polymers.

37. The method according to any of Clauses 31 to 36, wherein the first and second dyes are conjugates of a dye moiety and a specific binding member.

38. The method according to Clause 37, wherein the specific binding member comprises an antibody or binding fragment thereof.

39. The method according to any of Clauses 31 to 38, wherein the first and second high surface area solid supports have a surface area that is 0.5 $mm^2$ or more.

40. The method according to any of Clauses 31 to 39, wherein the first and second high surface area solid supports have a longest dimension ranging from 1 to 5 mm.

41. The method according to any of Clauses 31 to 40, wherein the first and second high surface area solid supports are porous.

42. The method according to Clause 41, wherein the first and second high surface area solid supports have a porosity ranging from 5μ to 90μ.

43. The method according to any of Clauses 31 to 42, wherein the first and second high surface area solid supports are fabricated from an inert material.

44. The method according to Clause 43, wherein the inert material is selected from a plastic, a glass and a ceramic.

45. The method according to Clause 44, wherein the inert material is a plastic.

46. The method according to any of Clauses 31 to 45, wherein the device comprises three or more distinct dried dye compositions each comprising a dye stably associated with a high surface area solid support.

47. The method according to any of Clauses 31 to 46, wherein the container is configured to hold a volume ranging from 0.1 ml to 250 ml.

48. The method according to Clause 47, wherein the container is a vial.

49. The method according to Clause 47, wherein the container is a well of a multi-well plate.

50. The method according to any of Clauses 31 to 49, wherein the container is sealed.

51. The method according to any of Clauses 31 to 50, wherein distinct first and second dried dye compositions are retained at a location of the container by a retainer.

52. The method according to Clause 51, wherein the retainer comprises a metal retainer.

53. The method according to any of Clauses 31 to 49, wherein the method further comprises assaying the reconstituted dye composition.
54. The method according to Clause 53, wherein the assaying comprises flow cytometrically analyzing the reconstituted dye composition.
55. The method according to any of Clauses 31 to 54, wherein the method further comprises storing the reconstituted dye composition for a period of time.
56. The method according to any of Clauses 31 to 55, wherein the method further comprises shipping the reconstituted dye composition to a remote location.
57. A method of making a reagent device, the method comprising:
   positioning distinct first and second dried dye compositions into a container, wherein:
      the first dried dye composition comprises a first dye stably associated with a first high surface area solid support; and
      the second dried dye composition comprises a second dye stably associated with a second high surface area solid support; to produce the reagent device.
58. The method according to Clause 57, wherein the first and second dyes differ from each other by at least one of excitation and emission maxima.
59. The method according to any of Clauses 57 to 58, wherein the first and second dyes are first and second polymeric dyes.
60. The method according to Clause 59, wherein the first and second polymeric dyes are water soluble conjugated polymers.
61. The method according to any of Clauses 57 to 60, wherein the first and second dyes are conjugates of a dye moiety and a specific binding member.
62. The method according to Clause 61, wherein the specific binding member comprises an antibody or binding fragment thereof.
63. The method according to any of Clauses 57 to 62, wherein the first and second high surface area solid supports have a surface area that is 0.5 mm$^2$ or more.
64. The method according to any of Clauses 57 to 63, wherein the first and second high surface area solid supports have a longest dimension ranging from 1 to 5 mm.
65. The method according to any of Clauses 57 to 64, wherein the first and second high surface area solid supports are porous.
66. The method according to Clause 65, wherein the first and second high surface area solid supports have a porosity ranging from 5μ to 90μ.
67. The method according to any of Clauses 57 to 66, wherein the first and second high surface area solid supports are fabricated from an inert material.
68. The method according to Clause 67, wherein the inert material is selected from a plastic, a glass and a ceramic.
69. The method according to Clause 68, wherein the inert material is a plastic.
70. The method according to any of Clauses 57 to 66, wherein the method further comprises positioning in the container a distinct third dried dye composition comprising a third dye stably associated with a third high surface area solid support.
71. The method according to any of Clauses 57 to 70, wherein the container is configured to hold a volume ranging from 0.1 ml to 250 ml.
72. The method according to Clause 71, wherein the container is a vial.
73. The method according to Clause 71, wherein the container is a well of a multi-well plate.
74. The method according to any of Clauses 72 to 73, wherein the method further comprises sealing the container.
75. The method according to any of Clauses 57 to 74, wherein the method further comprises retaining the distinct first and second dried dye compositions at a location of the container by a retainer.
76. The method according to Clause 75, wherein the retainer comprises a metal retainer.
77. The method according to any of Clauses 57 to 76, wherein the method further comprises positioning a set of standard fluorescently labelled particles into the container.
78. The method according to Clause 77 wherein the set of standard fluorescently labelled particles comprises glass beads.
79. A kit comprising:
   (a) a reagent device comprising:
   (i) a container; and
   (ii) distinct first and second dried dye compositions present in the container, wherein:
      the first dried dye composition comprises a first dye stably associated with a first high surface area solid support; and
      the second dried dye composition comprises a second dye stably associated with a second high surface area solid support; and
   (b) a packaging configured to hold the reagent device.
80. The kit according to Clause 79, wherein the first and second dyes differ from each by at least one of excitation and emission maxima.
81. The kit according to Clauses 79 or 80, wherein the first and second dyes are first and second polymeric dyes.
82. The kit according to Clause 81, wherein the first and second polymeric dyes are water soluble conjugated polymers.
83. The kit according to any of Clauses 79 to 82, wherein the first and second dyes are conjugates of a dye moiety and a specific binding member.
84. The kit according to Clause 83, wherein the specific binding member comprises an antibody or binding fragment thereof.
85. The kit according to any of Clauses 79 to 84, wherein the first and second high surface area solid supports have a surface area that is 0.5 mm$^2$ or more.
86. The kit according to any of Clauses 79 to 85, wherein the first and second high surface area solid supports have a longest dimension ranging from 1 to 5 mm.
87. The kit according to any of Clauses 79 to 86, wherein the first and second high surface area solid supports are porous.
88. The kit according to Clause 87, wherein the first and second high surface area solid supports have a porosity ranging from 5μ to 90μ.
89. The kit according to any of Clauses 79 to 88, wherein the first and second high surface area solid supports are fabricated from an inert material.
90. The kit according to Clause 89, wherein the inert material is selected from a plastic, a glass and a ceramic.
91. The kit according to Clause 90, wherein the inert material is a plastic.
92. The kit according to any of Clauses 79 to 91, wherein the device comprises three or more distinct dried dye compositions each comprising a dye stably associated with a high surface area solid support.

93. The kit according to any of Clauses 79 to 92, wherein the container is configured to hold a volume ranging from 0.1 ml to 250 ml.
94. The kit according to Clause 93, wherein the container is a vial.
95. The kit according to Clause 93, wherein the container is a well of a multi-well plate.
96. The kit according to any of Clauses 79 to 95, wherein the container is sealed.
97. The kit according to any of Clauses 79 to 96, wherein distinct first and second dried dye compositions are retained at a location of the container by a retainer.
98. The kit according to Clause 97, wherein the retainer comprises a metal retainer.
99. The kit according to any of Clauses 73 to 98, wherein the kit comprises a set of standard fluorescently labelled particles.
100. A reagent device comprising:
a container comprising a dried dye composition comprising one or more dyes stably associated with a high surface area solid support that is not stably associated with any surface of the container.
101. The device according to Clause 100, wherein the dried dye composition comprises a single dye.
102. The device according to Clause 100, wherein the dried dye composition comprises two or more dyes.
103. The device according to any of Clauses 100 to 102, wherein the one or more dyes are conjugates of a dye moiety and a specific binding member.
104. The device according to Clause 103, wherein the specific binding member comprises an antibody or binding fragment thereof.
105. The device according to any of Clauses 100 to 104, wherein the high surface area solid support has a surface area that is 0.5 mm$^2$ or more.
106. The device according to any of Clauses 100 to 105, wherein the high surface area solid support has a longest dimension ranging from 1 to 5 mm.
107. The device according to any of Clauses 100 to 106, wherein the high surface area solid support is porous.
108. The device according to Clause 107, wherein the high surface area solid support has a porosity ranging from 5µ to 90µ.
109. The device according to any of Clauses 100 to 108, wherein the high surface area solid support is fabricated from an inert material.
110. The device according to Clause 109, wherein the inert material is selected from a plastic, a glass and a ceramic.
111. The device according to Clause 110, wherein the inert material is a plastic.
112. The device according to any of Clauses 100 to 111, wherein the device comprises two or more dried dye compositions.
113. The device according to Clause 112, wherein the device comprises between 3 and 100 dried dye compositions.
114. The device according to any of Clauses 112 to 113, wherein the dried dye compositions in the container are identical.
115. The device according to any of clauses 112 to 113, wherein the dried dye compositions comprise at least two different dried dye compositions.
116. The device according to any of the preceding clauses, wherein the container is a vial.
117. The device according to any of Clauses 100 to 115, wherein the container is a well of a multi-well plate.
118. The device according to any of Clauses 100 to 115, wherein the container is a bottle.
119. The device according to any of Clauses 100 to 115, wherein the device is a dispenser.
120. The device according to any of Clauses 100 to 119, wherein the dried dye composition is retained at a location of the container by a retainer.
121. The device according to Clause 120, wherein the retainer comprises a metal retainer.
122. The device according to Clause 120, wherein the retainer comprises a mesh.
123. A method comprising:
positioning a volume of a liquid into a container comprising a dried dye composition comprising one or more dyes stably associated with a high surface area solid support that is not stably associated with any surface of the container to produce a reconstituted dye mixture in the container.
124. The method according to Clause 123, wherein the dried dye composition comprises a single dye.
125. The method according to Clause 123, wherein the dried dye composition comprises two or more dyes.
126. The method according to any of Clauses 123 to 125, wherein the one or more dyes are conjugates of a dye moiety and a specific binding member.
127. The method according to Clause 126, wherein the specific binding member comprises an antibody or binding fragment thereof.
128. The method according to any of Clauses 123 to 127, wherein the high surface area solid support has a surface area that is 0.5 mm$^2$ or more.
129. The method according to any of Clauses 123 to 128, wherein the high surface area solid support has a longest dimension ranging from 1 to 5 mm.
130. The method according to any of Clauses 123 to 129, wherein the high surface area solid support is porous.
131. The method according to Clause 130, wherein the high surface area solid support has a porosity ranging from 5µ to 90µ.
132. The method according to any of Clauses 123 to 131, wherein the high surface area solid support is fabricated from an inert material.
133. The method according to Clause 132, wherein the inert material is selected from a plastic, a glass and a ceramic.
134. The method according to Clause 133, wherein the inert material is a plastic.
135. The method according to any of Clauses 123 to 134, wherein the container is a vial.
136. The method according to any of Clauses 123 to 134, wherein the container is a well of a multi-well plate.
137. The method according to any of Clauses 123 to 136, wherein the method further comprises placing the dried dye composition into the container.
138. The method according to Clause 137, wherein the method further comprises obtaining the dried dye composition from a source comprising multiple dried dye compositions.
139. The method according to Clause 138, wherein the source comprises a bottle.
140. The method according to Clause 138, wherein the source comprises a dispenser.
141. The method according to any of Clauses 123 to 140, wherein the liquid comprises a biological sample.
142. The method according to Clause 141, wherein the biological sample comprises whole blood or a fraction thereof.
143. The method according to any of Clauses 123 to 142, wherein the method further comprises assaying the reconstituted dye composition.

144. The method according to Clause 143, wherein the assaying comprises flow cytometrically analyzing the reconstituted dye composition.
145. A method of making a reagent device, the method comprising:
positioning a dried dye composition comprising a dye stably associated with a high surface area solid support into a container to produce the reagent device, wherein the dried dye composition is not stably associated with any surface of the container.
146. The method according to Clause 145, wherein the dried dye composition comprises a single dye.
147. The method according to Clause 145, wherein the dried dye composition comprises two or more dyes.
148. The method according to any of Clauses 145 to 147, wherein the one or more dyes are conjugates of a dye moiety and a specific binding member.
149. The method according to Clause 148, wherein the specific binding member comprises an antibody or binding fragment thereof.
150. The method according to any of Clauses 145 to 149, wherein the high surface area solid support has a surface area that is 0.5 mm$^2$ or more.
151. The method according to any of Clauses 145 to 150, wherein the high surface area solid support has a longest dimension ranging from 1 to 5 mm.
152. The method according to any of Clauses 145 to 151, wherein the high surface area solid support is porous.
153. The method according to Clause 152, wherein the high surface area solid support has a porosity ranging from 5µ to 90µ.
154. The method according to any of Clauses 145 to 153, wherein the high surface area solid support is fabricated from an inert material.
155. The method according to Clause 154, wherein the inert material is selected from a plastic, a glass and a ceramic.
156. The method according to Clause 155, wherein the inert material is a plastic.
157. The method according to any of Clauses 145 to 156, wherein the container is a vial.
158. The method according to any of Clauses 145 to 156, wherein the container is a well of a multi-well plate.
159. The method according to any of Clauses 145 to 156, wherein the method comprises multiple dried dye compositions into the container.
160. The method according to Clause 159, wherein the container comprises a bottle.
161. The method according to Clause 159, wherein the container comprises a dispenser.
162. A kit comprising:
a container comprising a dried dye composition comprising one or more dyes stably associated with a high surface area solid support that is not stably associated with any surface of the container; and
a packaging configured to hold the container.
163. The kit according to Clause 162, wherein the container comprises multiple dried dye compositions.
164. The kit according to Clause 163, wherein the container comprises from 2 to 100 dried dye compositions.
165. The kit according to any of Clauses 162 to 164, wherein the container is a bottle.
166. The kit according to Clause 165, wherein the container comprises an instrument for removing a dried dye composition from the container.
167. The kit according to Clause 166, wherein the instrument comprises a tweezer.
168. The kit according to Clause 167, wherein the tweezer comprises a vacuum tweezer.
169. The kit according to any of Clauses 162 to 168, wherein the kit further comprises a vial.
170. The kit according to any of Clauses 162 to 164, wherein the container comprises a multi-well plate.
171. The kit according to Clause 170, wherein the multi-well plate comprises a mesh insert.
172. The kit according to any of Clauses 170 and 171, wherein the multi-well plate is sealed.
173. The kit according to any of Clauses 162 to 172, wherein the dried dye composition comprises a single dye.
174. The kit according to any of Clauses 162 to 172, wherein the dried dye composition comprises two or more dyes.
175. The kit according to any of Clauses 162 to 174, wherein the one or more dyes are conjugates of a dye moiety and a specific binding member.
176. The kit according to Clause 175, wherein the specific binding member comprises an antibody or binding fragment thereof.
177. The kit according to any of Clauses 162 to 176, wherein the high surface area solid support has a surface area that is 0.5 mm$^2$ or more.
178. The kit according to any of Clauses 162 to 177, wherein the high surface area solid support has a longest dimension ranging from 1 to 5 mm.
179. The kit according to any of Clauses 162 to 178, wherein the high surface area solid support is porous.
180. The kit according to Clause 179, wherein the high surface area solid support has a porosity ranging from 5µ to 90µ.
181. The kit according to any of Clauses 162 to 180, wherein the high surface area solid support is fabricated from an inert material.
182. The kit according to Clause 181, wherein the inert material is selected from a plastic, a glass and a ceramic.
183. The kit according to Clause 182, wherein the inert material is a plastic.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of embodiments of the present disclosure. It will be appreciated that those skilled in the art will be able to devise various arrangements which, although not explicitly described or shown herein, embody the principles of embodiments of the present disclosure and are included within its spirit and scope. Furthermore, all examples and conditional language recited herein are principally intended to aid the reader in understanding the principles of embodiments of the present disclosure being without limitation to such specifically recited examples and conditions. Moreover, all statements herein reciting principles, aspects, and embodiments of embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the embodiments of the present disclosure, therefore, is not intended to be limited to the exemplary embodiments shown and described herein. Rather, the scope and spirit of embodiments of the present disclosure are embodied by the appended claims.

What is claimed is:

1. A method comprising:
positioning a volume of a liquid into a liquid container comprising:
distinct first and second dried dye compositions within the liquid container, wherein:
the first dried dye composition comprises a first dye and a first high surface area solid support; and
the second dried dye composition comprises a second dye and a second high surface area solid support; and
wherein:
the first and second high surface area solid supports have a surface area of 0.5 mm$^2$ or more;
the first and second dyes differ from each other by at least one of excitation maxima and emission maxima;
the first and second dried dye compositions move freely relative to the surface of the liquid container; and
the first and second dyes separate from the first and second high surface area solid supports, respectively, following addition of a liquid to the liquid container;
to produce a reconstituted dye composition in the container; and
removing the reconstituted dye composition from the container.

2. The method according to claim 1, wherein the first dried dye composition comprises a single dye.

3. The method according to claim 1, wherein the first dried dye composition comprises two or more dyes.

4. The method according to claim 1, wherein the second dried dye composition comprises a single dye.

5. The method according to claim 1, wherein the second dried dye composition comprises two or more dyes.

6. The method according to claim 1, wherein the liquid comprises a biological sample.

7. The method according to claim 6, wherein the biological sample comprises whole blood or a fraction thereof.

8. The method according to claim 1, wherein the method further comprises assaying the reconstituted dye composition.

9. A reagent device comprising:
a liquid container: and
distinct first and second dried dye compositions with the liquid container, wherein:
the first dried dye composition comprises a first dye and a first high surface area solid support; and
the second dried dye composition comprises a second dye and a second high surface area solid support;
wherein:
the first and second high surface area solid supports have a surface area of 0.5 mm$^2$ or more;
the first and second dyes differ from each other by at least one of excitation maxima and emission maxima;
the first and second dried dye compositions move freely relative to the surface of the liquid container; and
the first and second dyes separate from the first and second high surface area solid supports, respectively, following addition of a liquid to the liquid container.

10. The device according to claim 9, wherein the first and second dyes are first and second polymeric dyes.

11. The device according to claim 10, wherein the first and second polymeric dyes are water soluble conjugated polymers.

12. The device according to claim 9, wherein the first and second dyes are conjugates of a dye moiety and a specific binding member.

13. The device according to claim 12, wherein the specific binding member comprises an antibody or binding fragment thereof.

14. The device according to claim 9, wherein the liquid container is sealed.

15. The device according to claim 9, wherein distinct first and second dried dye compositions are retained at a location of the liquid container by a retainer.

16. The device according to claim 15, wherein the retainer comprises a metal retainer.

17. The reagent device according to claim 9, wherein the liquid container is selected from the group consisting of: a vial, a test tube, a well of a multi-well plate, a bottle and a cannister.

18. The device according to claim 9, wherein the first and second high surface area solid supports have a porosity between 5 μm and 90 μm.

19. The device according to claim 9, wherein the first and second dried dye compositions are lyophilized dye compositions.

20. A reagent device comprising:
a liquid container comprising a dried dye composition comprising one or more polymeric dyes and a high surface area solid support that moves freely relative to a surface of the container, wherein the high surface area solid support has a surface area of 0.5 mm$^2$ or more and the polymeric dye separates from the high surface area solid support following addition of a liquid to the liquid container.

21. The device according to claim 20, wherein the high surface area solid support has a porosity between 5 μm and 90 μm.

* * * * *